(12) United States Patent
Payne

(10) Patent No.: US 8,283,444 B2
(45) Date of Patent: *Oct. 9, 2012

(54) NON-VIRAL DELIVERY OF COMPOUNDS TO MITOCHONDRIA

(75) Inventor: R. Mark Payne, Clemons, NC (US)

(73) Assignee: Wake Forest University, Winston-Salem, NC (US)

( * ) Notice: Subject to any disclaimer, the term of this patent is extended or adjusted under 35 U.S.C. 154(b) by 953 days.

This patent is subject to a terminal disclaimer.

(21) Appl. No.: 10/972,222

(22) Filed: Oct. 22, 2004

(65) Prior Publication Data

US 2005/0169904 A1 Aug. 4, 2005

Related U.S. Application Data

(60) Provisional application No. 60/514,892, filed on Oct. 24, 2003.

(51) Int. Cl.
*C07K 1/00* (2006.01)
*A61K 39/21* (2006.01)
*A61K 38/44* (2006.01)

(52) U.S. Cl. ............... 530/350; 424/93.1; 424/94.4

(58) Field of Classification Search ............... None
See application file for complete search history.

(56) References Cited

U.S. PATENT DOCUMENTS

| | | | |
|---|---|---|---|
| 6,348,185 B1 | 2/2002 | Piwnica-Worms | |
| 6,821,948 B1 * | 11/2004 | Braun et al. | 514/2 |
| 7,329,638 B2 * | 2/2008 | Yang et al. | 514/2 |
| 2001/0008771 A1 | 7/2001 | Seibel et al. | |
| 2003/0026781 A1 | 2/2003 | Anderson et al. | |
| 2003/0161809 A1 * | 8/2003 | Houston et al. | 424/85.2 |
| 2004/0072774 A1 * | 4/2004 | Manfredi et al. | 514/44 |
| 2007/0196334 A1 * | 8/2007 | Khan | 424/93.2 |
| 2011/0190224 A1 | 8/2011 | Payne | |
| 2011/0245146 A1 | 10/2011 | Payne | |

OTHER PUBLICATIONS

Becker-Hapak et al. ("TAT-Mediated Protein Transduction into Mammalian Cells", Methods, (2001) 24, p. 247-256).*
Shimizu et al in "BH4 domain of antiapoptotic Bcl-2 family members closes voltage-dependent anion channel and inhibits apoptotic mitochondrial changes and cell death" in PNAS, Mar. 28, 2000, vol. 97: pp. 3100-3105.*
Thornton et al in "Import, Processing, and Two-dimensional NMR Structure of a Linker-deleted Signal Peptide of Rat Liver Mitochondrial Aldehyde Dehydrogenase": JBC, vol. 268, 1993, pp. 19906-19914, entire document).*
Shokolenko et al "TAT-mediated protein transduction and targeted delivery of fusion proteins into mitochondria of breast cancer cells" (DNA Repair, vol. 4, 2005, pp. 511-518).*
Taylor et al in "Crystal structures of mitochondrial processing peptidase reveal the mode for specific cleavage of import signal sequences" (Structure, Jul. 2001 vol. 9, No. 7: pp. 615-625).*
IJlst et al in "Common Missense Mutation G1528C in Long-Chain 3-Hydroxyacyl-CoA Dehydrogenase Deficiency: Characterization and Expression of the Mutant Protein, Mutation Analysis on Genomic DNA and Chromosomal Localization of the Mitochondrial Trifunctional Protein a Subunit Gene" (J Clin Invest. Aug. 15, 1996; vol. 98, No. 4: pp. 1028-1033).*
Muratovska et al in "Targeting large molecules to mitochondria" (Advanced Drug Delivery Reviews: 2001, vol. 49, pp. 189-198).*
Zeviani et al in "Nuclear genes in mitochondrial disorders" (Curr Opin Genet & Dev: Jun. 2003; available online Apr. 29, 2003, vol. 13, pp. 262-270).*
Dietz et al (Molecular & Cellular Neuroscience, 2002: vol. 21, pp. 29-37).*
Shimokata et al in "Substrate Recognition by Mitochondrial Processing Peptidase toward the Malate Dehydrogenase Precursor" (J Biochem, 1997: vol. 122, pp. 1019-1023).*
Gaizo et al.; "Targeting proteins to mitochondria using TAT" *Molecular Genetics and Metabolism* 80 170-180 (2003).
Gaizo et al.; "A Novel TAT-Mitochondrial Signal Sequence Fusion Protein Is Processed, Stays in Mitochondria, and Crosses the Placenta" *Molecular Therapy* 7:6 720-730 (2003).
Moore et al.; "Transactivator of Transcription Fusion Protein Transduction Causes Membrane Inversion" *The Journal of Biological Chemistry* 279:31 32541-32544 (2004).
International Search Resort for PCT/US04/35009; Date of Mailing May 9, 2005.
International Preliminary Report on Patentability for International Application PCT/US2004/035009, mailed May 4, 2006.
Rapoport, M., et al., TAT-mediated delivery of LAD restores pyruvate dehydrogenase complex activity in the mitochondria of patients with LAD deficiency, Mol. Ther..16(4): 691-7, American Society of Gene Therapy, Apr. 2008.
Ross, M.F., and Murphy, M.P., Cell-penetrating peptides are excluded from mitochondrial matrix, Biochem. Soc. Trans. (2004) 32(6):1072 -4, Biochemical Society, Dec. 2004.
Ross, M.F., et al., Cell-penetrating peptides do not cross mitochondrial membranes even when conjugated to a lipophilic cation; evidence against direct passage through phospholipid bilayers, Biochem. J. 383:457-68, Biochemical Society, Nov. 2004.
Watkins et al, "Cellular uptake, distribution and cytotoxicity of the hydrophobic cell penetrating peptide sequence PFVYLI linked to the proapoptotic domain peptide PAD," J. Con. Rel. 140:237-244 (2009).
U.S. Appl. No. 13/082,526, filed Apr. 8, 2011; Office Action mailed Oct. 7, 2011.
U.S. Appl. No. 13/082,528; filed Apr. 8, 2011; Office Action mailed Oct. 11, 2011.

* cited by examiner

*Primary Examiner* — Jim Ketter
*Assistant Examiner* — Catherine Hibbert
(74) *Attorney, Agent, or Firm* — Myers Bigel Sibley & Sajovec, P.A.

(57) ABSTRACT

A conjugate comprises: (a) a mitochondrial membrane-permeant peptide; (b) an active agent or compound of interest such as a detectable group or mitochondrial protein or peptide; and (c) a mitochondrial targeting sequence linking said mitochondrial membrane-permeant peptide and said active mitochondrial protein or peptide. The targeting sequence is one which is cleaved within the mitochondrial matrix, and not cleaved within the cellular cytoplasm, of a target cell into which said compound is delivered. Methods of use of such compounds are also described.

1 Claim, 8 Drawing Sheets

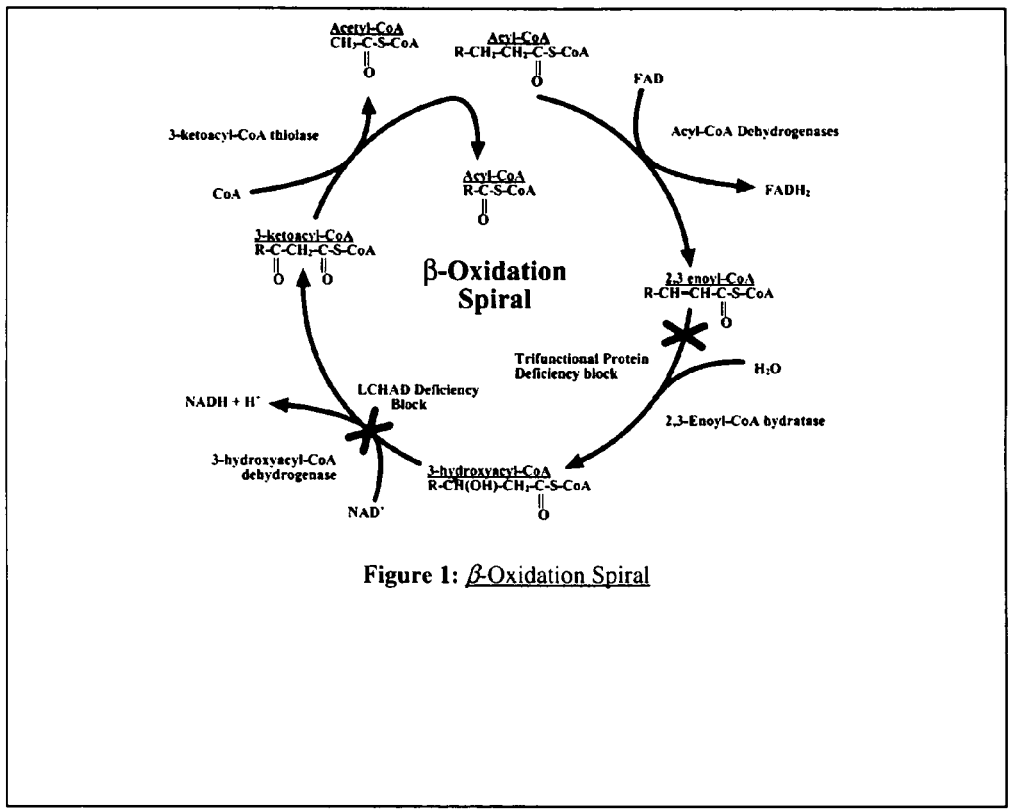
Figure 1: *β-Oxidation Spiral*
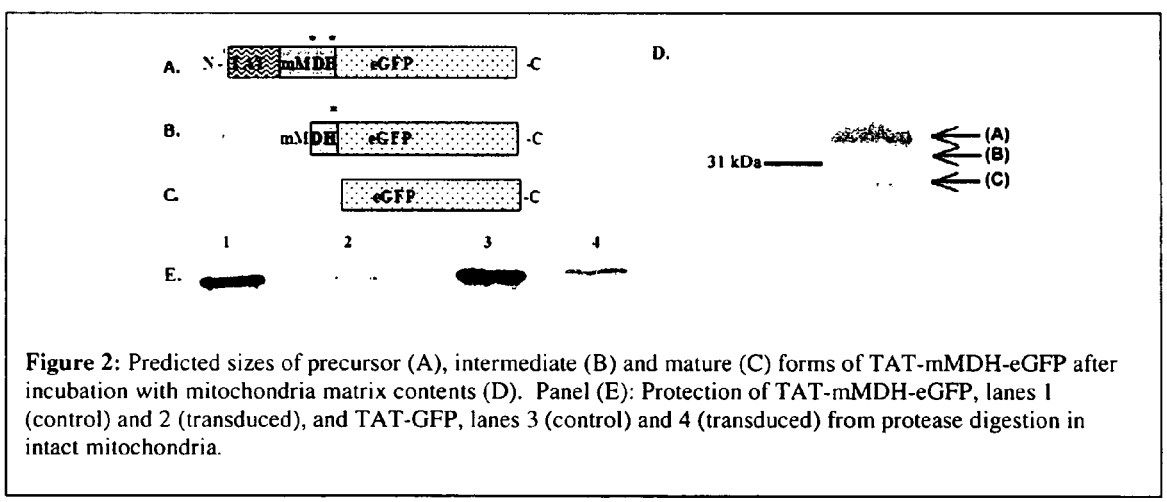
Figure 2: Predicted sizes of precursor (A), intermediate (B) and mature (C) forms of TAT-mMDH-eGFP after incubation with mitochondria matrix contents (D). Panel (E): Protection of TAT-mMDH-eGFP, lanes 1 (control) and 2 (transduced), and TAT-GFP, lanes 3 (control) and 4 (transduced) from protease digestion in intact mitochondria.

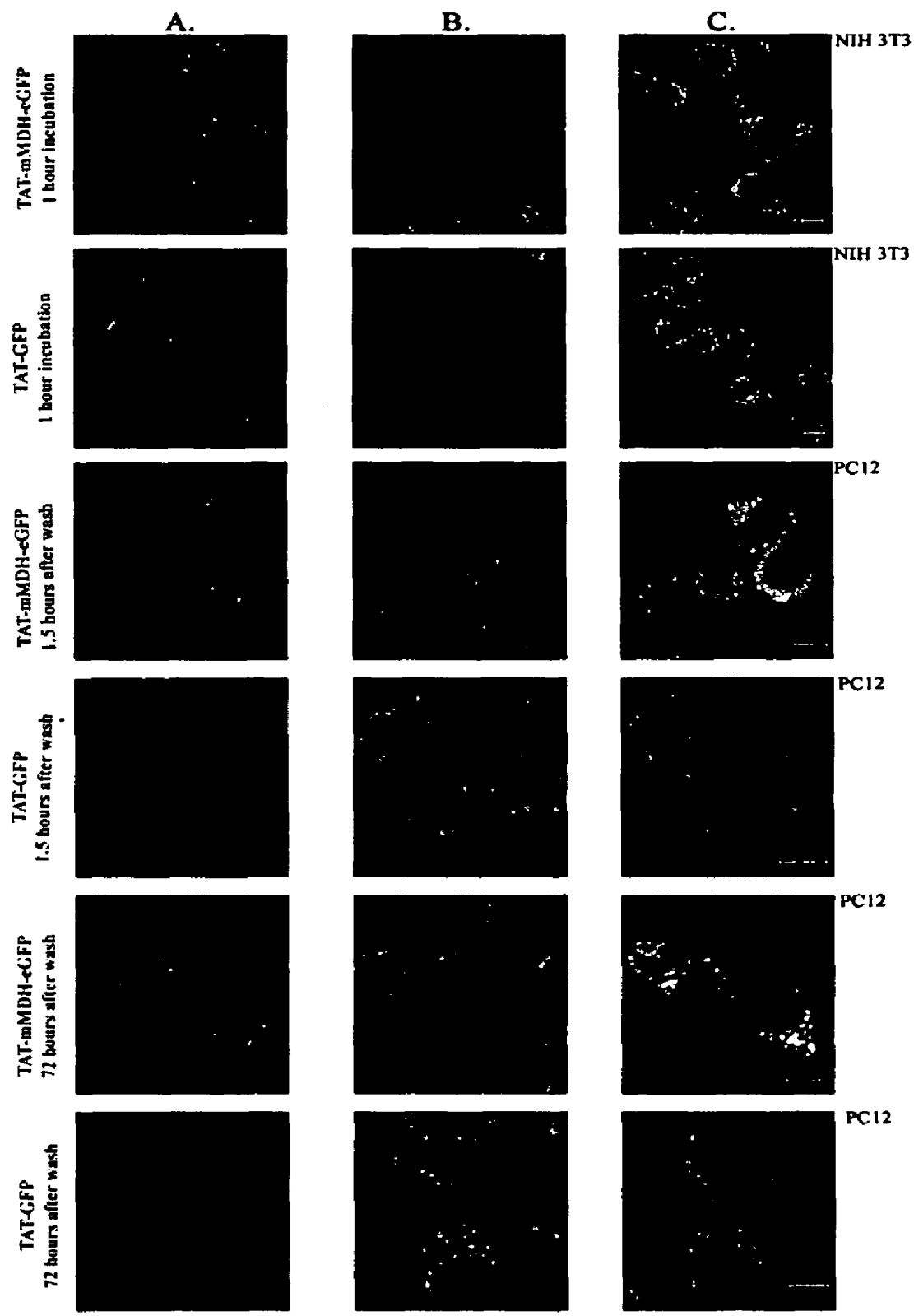
Figure 3: TAT-mMDH-eGFP, but not TAT-GFP, co-localizes to mitochondria.

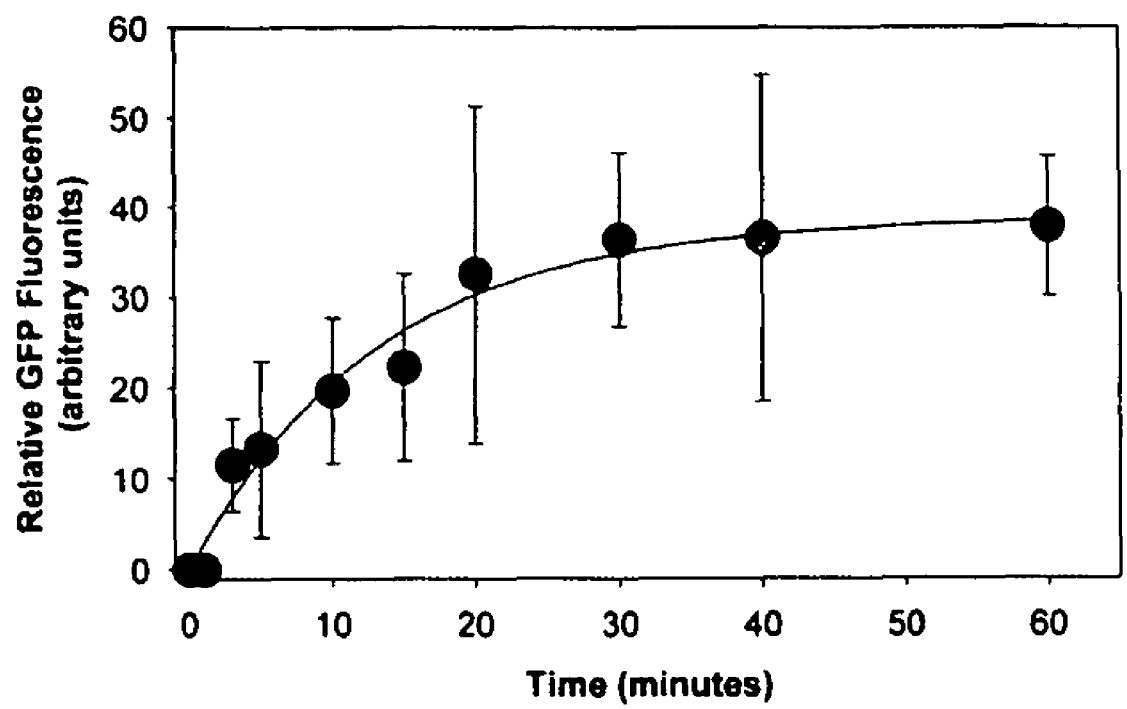
Figure 4: Kinetics of TAT fusion protein transduction.

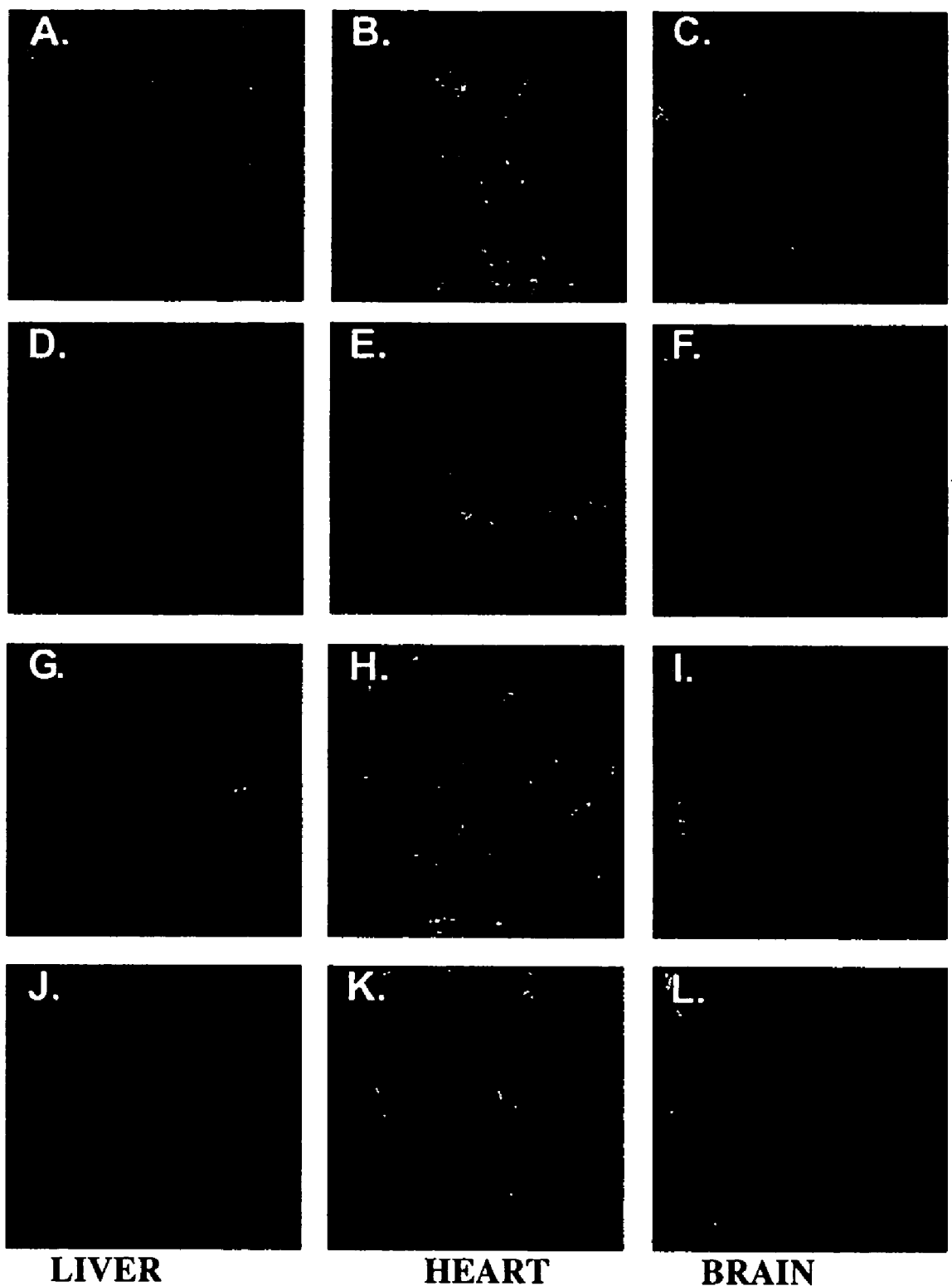
Figure 5: Mouse tissues after TAT-fusion protein

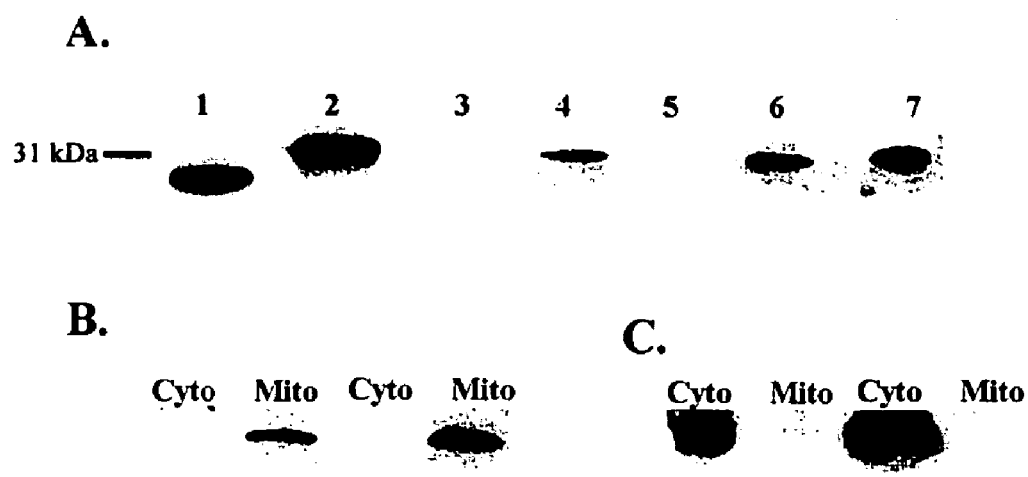
Figure 6: Intracellular location of TAT-mMDH-eGFP and TAT-GFP 5 days after injection into mice.

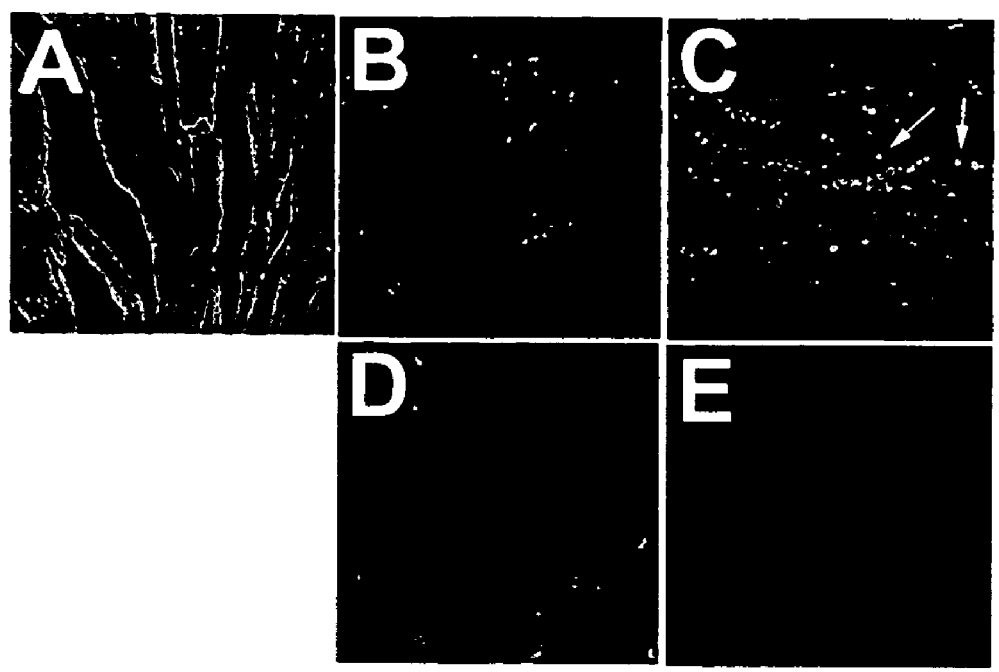
Figure 7: Placental transfer.
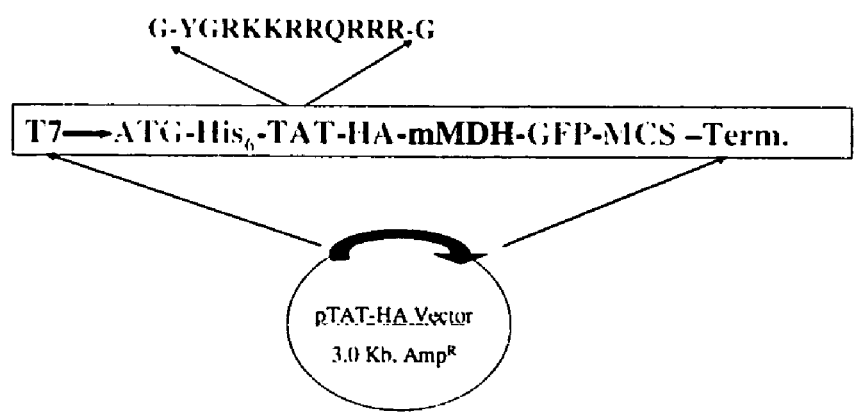
Figure 8: Construction of TAT-mMDH-eGFP Fusion Protein.

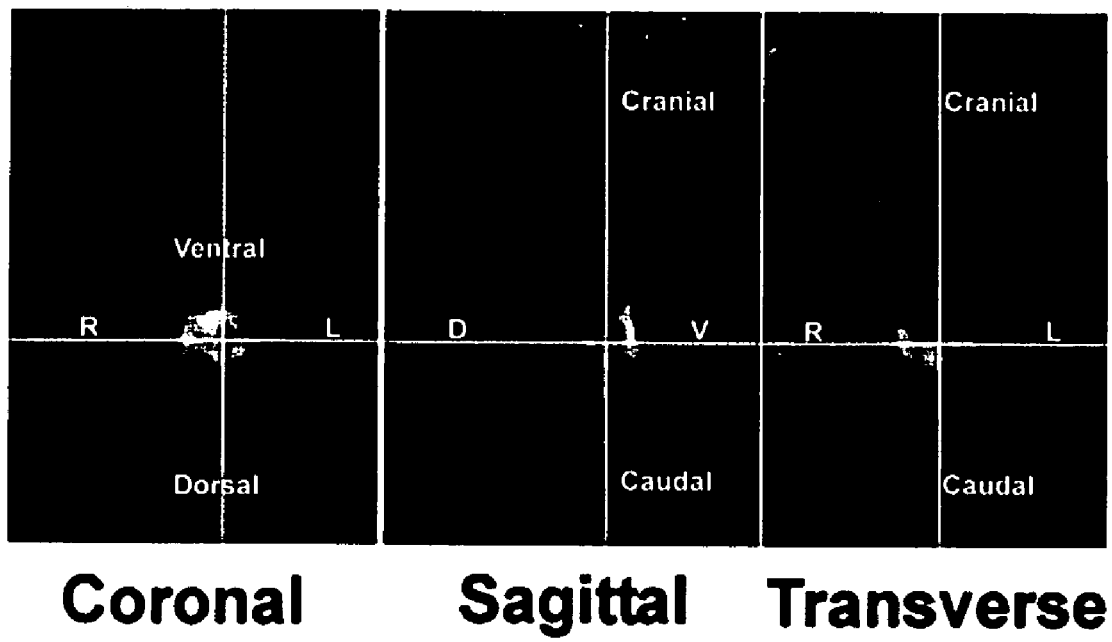
Figure 9: PET Scan of mouse heart.
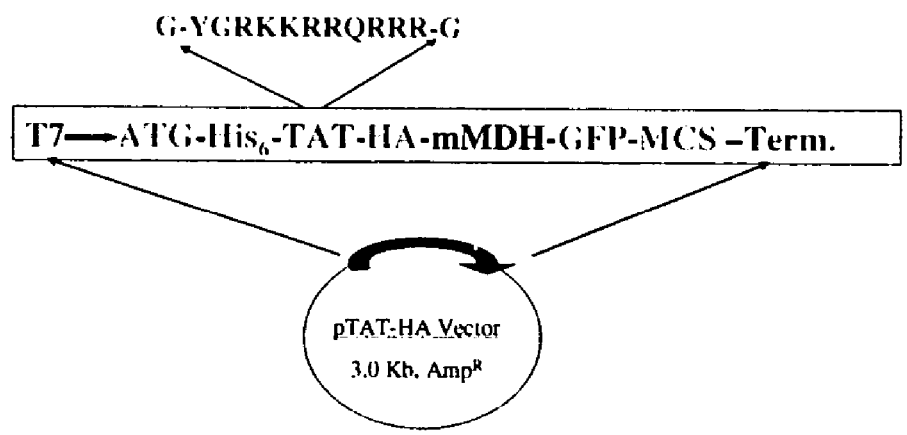
Figure 10: Construction of TAT-mMDH-eGFP Fusion Protein.

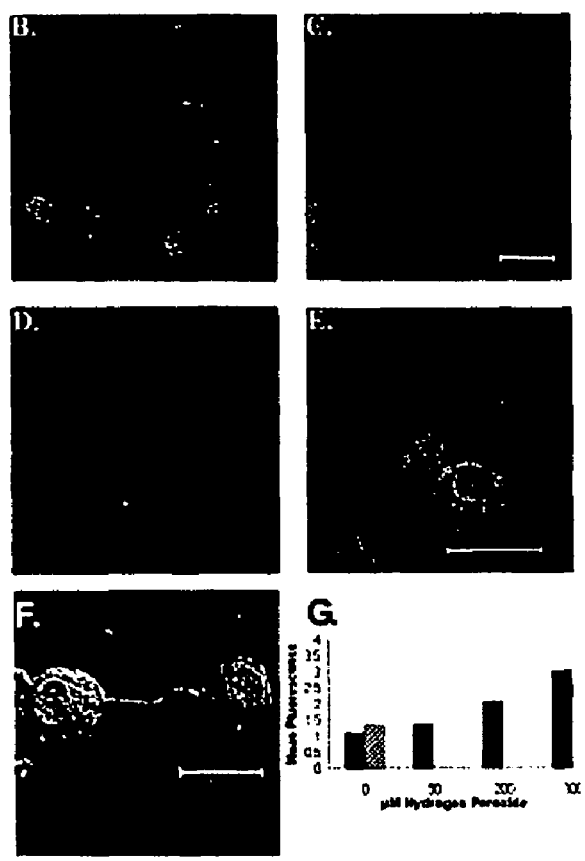
Figure 11. TAT-fusion protein transduction causes phosphatidylserine flip.
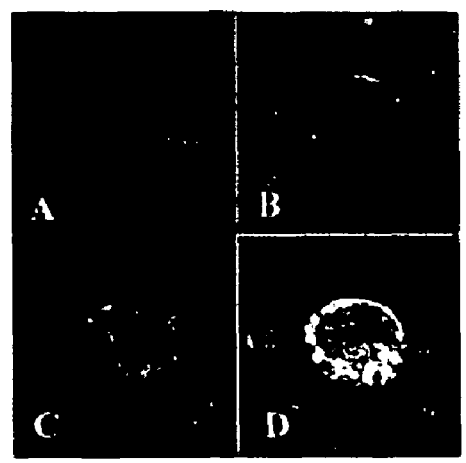
Figure 12: Transduction of human Frataxin into NIH 3T3 cells.

NON-VIRAL DELIVERY OF COMPOUNDS TO MITOCHONDRIA

RELATED APPLICATIONS

This application claims the benefit of U.S. Provisional Application Ser. No. 60/514,892 filed Oct. 24, 2003, the disclosure of which is incorporated by reference herein in its entirety.

GOVERNMENT SUPPORT

This invention was made with U.S. Government support under grant numbers RO1 DK55765 and RO1 DK67763 from the National Institutes of Health. The U.S. Government has certain rights to this invention.

FIELD OF THE INVENTION

The present invention concerns methods and compounds for the delivery of compounds, including detectable compounds, proteins and peptides, to mitochondria. The methods and compounds are useful for diagnostic purposes and for the treatment of mitochondrial diseases such as Friedreich's ataxia, human mitochondrial trifunctional protein deficiency, and Leber's Hereditary Optic Neuropathy.

BACKGROUND OF THE INVENTION

Mitochondria produce virtually all of the energy supply in tissues with high energy demands, and many diseases of impaired mitochondrial function have been described involving both mitochondrial and nuclear genomes (B. Robinson, *Journal of Bioenergetics & Biomembranes* 26:311-316 (1994); D. Wallace, *American Journal of Human Genetics* 57:201-223 (1995)). Of the hundreds of proteins that are found within mitochondria, the mitochondrial genome encodes only 13 of these and the rest must be imported from the cytosol (R. Jansen, *Human Reproduction* 15 Suppl 2:1-10 (2000); M. Douglas,. and M. Takeda, *Trends in Biochemical Sciences* 10:192-194 (1985)). Based on in vitro observations, proteins targeted to the mitochondria are thought to be completely synthesized in the cytoplasm and cross the mitochondrial membranes post-translationally (G. Schatz, and B. Dobberstein, *Science* 271:1519-1526(1996)). Proteins that are nuclearly encoded and targeted to the inner and outer membranes, inter-membrane space, or matrix, are aided by the use of presequences at the N-terminus of the precursor protein (G. Schatz, *Journal of Biological Chemistry* 271:31763-31766 (1996); A. Mayer et al. *Cell* 80:127-137(1995)). Most of these mitochondrial targeting sequences (MTS) consist of 10 to 70 amino acids that are removed by 1 or 2 proteolytic steps once inside the mitochondria. At the outer mitochondrial membrane the MTS is recognized by a receptor complex (OM37, OM70, or an OM37/OM70 complex), the presequence is passed to OM20, or an OM20/OM22 complex, and membrane translocation proceeds through the channel in the outer membrane translocation machinery (TOM complex) (T. Komiya, and K. Mihara, *Journal of Biological Chemistry* 271:22105-22110 (1996)). After translocation of the presequence across the outer membrane, a portion of the presequence is recognized by a receptor of the inner membrane (IM) translocation machinery (TIM complex) (M. Bauer, et al., *Cell* 87:33-41 (1996)). The precursor protein then proceeds through both the TOM and TIM complexes in conjunction with mitochondrial HSP70 and Tim44 on the matrix side of the IM. Import is driven by ATP hydrolysis of the HSP70 motor, and the transit peptide is cleaved by the mitochondrial processing peptidase (G. Isaya, et al., *Proceedings of the National Academy of Sciences of the United States of America* 89:8317-8321 (1992); T. Omura, *Journal of Biochemistry* 123:1010-1016 (1998)) Finally, the protein is deposited in the matrix or integrated into the IM (J. Berthold, et al., *Cell* 81:1085-1093(1995); C. Ungermann, et al., *EMBO Journal* 15:735-744 (1996)).

Both nuclear-encoded and mitochondrial-encoded proteins can be mutated, deleted, or be insufficient in amount, leading to functional problems (D. Wallace, *Scientific American* 277:40-47 (1997); C. Graff, et al., *Journal of Internal Medicine* 246:11-23 (1999)). Furthermore, there is now a growing body of information on how the compartmentation of mitochondrial proteins, and their function, can be disturbed by acquired conditions, such as aging, oxidative stress, and ischemia, and which may lead to disease or decreased tissue function (J. Rosenblum, et al., *Proceedings of the National Academy of Sciences of the United States of America* 93:4471-4473(1996); G. Davey, et al., *Journal of Biological Chemistry* 273:12753-12757 (1998)). One possible way to alleviate these problems is to deliver exogenous protein to mitochondria to replace the defective or deficient proteins. To date this has been very difficult with viral or nonviral vectors (R. Owen and T. Flotte, *Antioxidants & Redox Signaling* 3:451-460 (2001); Y. Bai, et al., *Journal of Biological Chemistry* 276:38808-38813 (2001); K. Nakada, et al., *Nature Medicine* 7:934-940 (2001); V. Weissig, and V. Torchilin, *Advanced Drug Delivery Reviews* 49:127-149 (2001); B. Seo, et al., *Proceedings of the National Academy of Sciences of the United States of America* 95:9167-9171 (1998)). In particular, viral-mediated gene transfer has been associated with poor transfection rates and the risk of death in patients (P. Noguchi, *N. Engl. J. Med.* 348:193-194 (2003). Non-viral techniques, such as liposome mediated gene transfer, have been even more disappointing when applied to vertebrate tissues.

Mitochondria are organelles that are vulnerable to damage for at least three reasons. First; mitochondria contain a limited genome, approximately 16 kb in humans. Thus, the majority of proteins essential for continued function must be imported into mitochondria. Defects in these nuclear encoded proteins result in human disease. Furthermore, diseases involving mitochondrial-encoded DNA present a special challenge for potential gene therapy because most of the proteins encoded are hydrophobic and lack a transit peptide. Thus, these proteins are difficult to keep in the unfolded conformation needed for import. This means their ability to respond appropriately in synthesizing new proteins after damaging conditions such as birth asphyxia, heart attack, stroke, or aging, is limited. Second, mitochondria lack histones and thus, do not have efficient mechanisms for protection and repair of DNA damage. Consequently, mutations within the mitochondrial DNA (mtDNA) are cumulative and result in disease, such as Leber's Hereditary Optic Neuropathy. Third, mitochondria contain a highly oxidative environment and generate 95% of the total superoxide radicals in the cell (A. Boveris, *Methods in Enzymology* 105:429-435 (1984)). Thus, oxidative damage to the mtDNA and proteins is constant and certain. Mitochondria have evolved protective mechanisms against this damage, such as mitochondrial superoxide dismutase; however, these can be overwhelmed by abnormal physiology with resultant overproduction of superoxide and damaging free radicals.

Given that many human diseases involve mitochondrial dysfunction, and there are currently no satisfactory methods to correct these defects, there is a need to develop techniques to screen for these defects and therapies to correct mitochondrial defects.

Background on Protein Transduction Domains (PTD). Delivery of drugs and therapeutic compounds is primarily limited by their ability to penetrate the cell membrane. The bioavailability of compounds targeted to intracellular sites depends on the conflicting requirements of being sufficiently polar for administration and distribution, yet non-polar enough to diffuse through the non-polar lipid bilayer of the cell (D. Begley, *Journal of Pharmacy & Pharmacology* 48:136-146 (1996)). In addition, the molecular weight of most drugs that can easily traverse the lipid membrane is approximately 500 Da (V. Levin, *Journal of Medicinal Chemistry* 23:682-684 (1980)). Thus, most successful compounds have narrow physical characteristics. Many promising drugs fail because they fall outside of this range and efforts to make them available may be toxic. In addition to this, many sites of action for presumed therapeutic compounds, such as enzymes or regulatory proteins, require processing and targeting of the compound once inside the cell.

To address these problems, delivery of a gene product into cells has been heavily investigated using both viral and non-viral vectors, as well as naked DNA and liposome-mediated gene transfer (V. Geromel, et al., *Antisense & Nucleic Acid Drug Development* 11:175-180 (2001); S. Francis, et al., *American Journal of PharmacoGenomics* 1:55-66 (2001); B. Cao, et al., *Microscopy Research & Technique* 58:45-51 (2002)). However, drawbacks with current 'gene therapies', such as viral toxicity and inefficient transfection rates, the immune response to viral vectors, and difficulty in creating the gene vector, have limited their usefulness in gene therapy (M. Rebolledo, et al., *Circulation Research* 83:738-74 (1998); T. Ritter, et al., *Biodrugs* 16:3-10 (2002)). Furthermore, localizing a gene product within the cell has been difficult. For example, attempts to deliver proteins to mitochondria within the cells to correct defects in their function have been limited (P. Seibel, et al., *Nucleic Acids Research* 23:10-17 (1995)). The use of mitochondrial targeting sequences to localize fusion proteins within mitochondria is not a new concept. Fusion proteins made with mitochondrial signal sequences have been transfected into cultured cells and shown to not only be targeted to mitochondria, but also processed, allowing for complete localization and functionality of the fused protein (C. Zhang, et al., *Biochemical & Biophysical Research Communications* 242:390-395 (1998); B. Seaton, and L. Vickery, *Archives of Biochemistry & Biophysics* 294:603-608 (1992)). However, the transfer of this technology to tissues in vivo has not been successful, in part, because of problems with delivery of the gene product.

Recently, a novel strategy for delivery of synthetic compounds has been described and is being actively investigated by both industry and academic researchers (R. Service, *Science* 288:28-29 (2000)). Positively charged, cationic peptides, are known to cross cell membranes independent of receptors or specific transport mechanisms (S. Schwarze, et al., *Science* 285:1569-1572 (1999); A. Ho, et al., *Cancer Research* 61:474-477 (2001);. M. Morris, et al., *Nature Biotechnology* 19:1173-1176 (2001); M. Pooga, et al., *FASEB Journal* 12:67-77 (1998); D. Derossi, et al., *Journal of Biological Chemistry* 271:18188-18193(1996); G. Pietersz, et al., *Vaccine* 19:1397-1405 (2001); G. Elliott, and P. O'Hare, *Cell* 88:223-233 (1997); W. Derer, et al., *FASEB Journal* 16:132-133 (2002); E. Will, et al., *Nucleic Acids Research* 30:e59 (2002); J. Rothbard, et al., *Journal of Medicinal Chemistry* 45:3612-3618 (2002); L. Chen, et al., *Chemistry & Biology* 8:1123-1129 (2001); P. Wender, et al., *Proceedings of the National Academy of Sciences of the United States of America* 97:13003-13008 (2000)). The transport involves protein transduction domains (PTD) that are highly charged, short peptides (~10 to 20 amino acids), containing basic amino acids (arginines and lysines), and that have the ability to form hydrogen bonds. The ability of PTD's to cross cell membranes is also concentration-dependent.

Multiple investigators have found that attachment of nucleic acids, peptides, and even large proteins to these PTD's will allow their transduction across all cell membranes in a highly efficient manner (S. Schwarze and S. Dowdy, *Trends in Pharmacological Sciences* 21 :45-48 (2000)). Three PTD's have been described which share the common characteristics of being potential DNA binding proteins: HIV-TAT, VP22, and Antennapedia (S. Schwarze, et al., *Science* 285:1569-1572 (1999); D. Derossi, et al., *Journal of Biological Chemistry* 271:18188-18193(1996); G. Elliott, and P. O'Hare, *Cell* 88:223-233 (1997)). Based on computer modeling and the prediction that these PTD's often have a strong a-helical character with a face of basically charged residues (arginines), investigators have begun to create synthetic peptides with greater ability to efficiently and quickly transduce across cell membranes. The exact mechanism of protein transduction is not known but is not receptor mediated and is independent of temperature making it unlikely that endocytosis or transporter mechanisms are involved (D. Mann and A. Frankel, *EMBO Journal* 10:1733-1739 (1991)). Furthermore, treatment of cells with drugs that inhibit cellular transport, such as brefeldin A (inhibits golgi transport), do not affect transduction of PTD's (G. Elliott, and P. O'Hare, *Cell* 88:223-233 (1997)).

Recently it was shown that the PTD derived from the HIV genome, HIV-TAT (trans-activator of transcription, "TAT"), has the ability to move attached peptides, large proteins, and nucleic acids across virtually all cell membranes, including brain, in a non-receptor mediated fashion (S. Schwarze, et al., *Science* 285:1569-1572 (1999); G. Cao, et al., *Journal of Neuroscience* 22:5423-5431 (2002); A. Gustafsson, et al., *Circulation* 106:735-739 (2002); H. Nagahara, et al., *Nature Medicine* 4:1449-1452 (1998)). The attached proteins are refolded into an active conformation once inside the cell and are biologically active. The full length TAT protein, originally described in 1988, by Green and Lowenstein, and is an 86 amino acid protein encoded by the HIV virus (S. Fawell, et al., *Proc.Natl.AcadSci.U.S.A.* 91:664-668 (1994); A. Frankel, and C. Pabo, *Cell* 55:1189-1193(1988); M. Green and P. Loewenstein, *Cell* 55:1179-1188(1988)). More specifically, an 11 amino acid arginine-and lysine-rich portion of the TAT sequence, YGRKKRRQRRR (SEQ ID NO:3), conjugated to peptides that do not normally cross membranes, is able to transduce across cell membranes and deliver a biologically active fusion protein to tissues. Furthermore, when a TAT-fusion protein was injected into mice for two weeks, there were no gross signs of neurological problems or system distress. Previously, TAT-fusion proteins were shown to be capable of delivering an active fusion protein that affects mitochondrial function, though in both cases, the fusion protein was not processed by the mitochondria. (G. Cao, et al., *Journal of Neuroscience* 22:5423-5431 (2002); A. Gustafsson, et al., *Circulation* 106:735-739 (2002)).

In summary, PTD's appear to offer a method for the efficient and rapid transport of highly charged, polar compounds across virtually all cell membranes and tissues in a concentration-dependent manner. This includes the mitochondrial membranes. These PTD's are well tolerated with only minimal detrimental effects seen at high concentrations in cell culture. However, because PTD-fusion proteins follow a concentration gradient, their use as therapeutic vehicles is limited by loss of the PTD-fusion protein from the cell unless the protein is bound or processed.

SUMMARY OF THE INVENTION

A first aspect of the present invention is a compound or conjugate comprising: (a) a mitochondrial membrane-permeant peptide; (b) an active agent or compound of interest such as a mitochondrial protein or peptide, nucleic acid, drug, or signaling agent; and (c) a mitochondrial targeting sequence linking said mitochondrial membrane-permeant peptide and said active mitochondrial protein or peptide. The targeting sequence is one which is cleaved within the mitochondrial matrix, and not cleaved within the cellular cytoplasm, of a target cell into which said compound is delivered.

A second aspect of the present invention is a composition comprising a compound or conjugate as described above in a pharmaceutically acceptable carrier.

A third aspect of the present invention is a method of delivering a compound of interest to the mitochondria of a cell comprising contacting a compound or conjugate as described above to a cell, or a tissue containing said cell, in vitro or in vivo so that said compound of interested is delivered into the mitochondria of said cell.

A further aspect of the present invention is a method of treating a mitochondrial disorder in a subject in need thereof, comprising administering a compound or conjugate as described above to said subject in an amount effective to treat said mitochondrial disorder.

A further aspect of the present invention is the use of a compound or conjugate as described above for the preparation of a composition or medicament for carrying out a method as described above.

The invention is explained in greater detail in the drawings herein and the specification set forth below.

BRIEF DESCRIPTION OF THE DRAWINGS

FIG. 1: β-Oxidation Spiral. The 3 enzymatic steps of the TFP are shown with blocks (red) occurring at 3-hydroxyacyl-CoA dehydrogenase (LCHAD) and before the hydratase reaction (complete TFP deficiency).

FIG. 2: Predicted sizes of precursor (A), intermediate (B) and mature (C) forms of TAT-mMDH-eGFP after incubation with mitochondria matrix contents (D). Panel (E): Protection of TAT-mMDH-eGFP, lanes 1 (control) and 2 (transduced), and TAT-GFP, lanes 3 (control) and 4 (transduced) from protease digestion in intact mitochondria.

FIG. 3: TAT-mMDH-eGFP, but not TAT-GFP, co-localizes to mitochondria. NIH 3T3 or differentiated PC12 cells, were incubated with 0.01 mg/ml of either TAT-mMDH-eGFP or TAT-GFP for 1 hour, and imaged at later times (left side of rows). Cells were then stained with CMX-Rosamine prior to analysis by confocal microscopy. The localization of GFP alone (green, column A) or CMX-Rosamine alone (red, column B) and co-staining (yellow, column C) is shown. Yellow stain indicates co-localization of GFP and CMX-Rosamine within mitochondria. Cell line is indicated on the right for each row. Micron bars indicating magnification are 10 microns and 5 microns in length for NIH 3T3 and PC12 cells, respectively, and all samples represent an N of 2.

FIG. 4: Kinetics of TAT fusion protein transduction. TAT-GFP transduces into PC12 cells with pseudo-first order kinetics. Cells were incubated with 0.01 mg/ml TAT-GFP for progressive times, images taken with the confocal microscope, and the average fluorescence minus background analyzed. The average relative fluorescence at each time point is plotted on the y axis. All points are the average of seven image fields. The solid line was obtained by fitting to an equation, $F=F_{max}[1-e^{-t/t1/2}]$, which yielded $F_{max}=38.8\pm2.0$ and $t_{1/2}=13.2\pm1.9$ min. The error bars represent the standard deviation.

FIG. 5: Mouse tissues after TAT-fusion protein. SVEV mice were injected ip with 2 mg/kg TAT-GFP or TAT-mMDH-eGFP and sacrificed 17 hours, or 5 days later. All comparable samples were scanned with the same pinhole and detector gain settings. A,B,C: TAT-mMDH-eGFP 17 hr after injection. D,E,F: TAT-GFP 17 hr after injection. G,H,I: TAT-mMDH-eGFP 5 d after injection. J,K,L: TAT-GFP 5 d after injection.

FIG. 6: Intracellular location of TAT-mMDH-eGFP and TAT-GFP 5 days after injection into mice. (A) 5 days post injection of TAT-mMDH-eGFP or TAT-GFP into SVEV mice, mitochondria (lanes 1 and 5), cytosolic (lanes 3 and 6), and mitochondrial wash (lane 4) fractions were isolated from liver and resolved along with purified TAT-mMDH-eGFP (lane 2) and TAT-GFP (lane 7) via SDS-PAGE. Proteins were transferred to nylon membranes and probed with antibodies against GFP. As controls, cytosolic and mitochondrial fractions were also probed with antibodies against cytochrome c oxidase subunit vb (B) and cathepsin L (C). Data are representative of results from two independent experiments. Cyto=cytosolic fraction and Mito=mitochondrial fraction.

FIG. 7: Placental transfer. Pregnant mice were injected ip with 2 mg/kg TAT-mMDH-eGFP at 18 d gestation and sacrificed 24 and 48 hr later. A) Maternal heart 24 hr post injection. B) Fetal heart 24 hr post maternal injection. C) Newborn pup heart 48 hr post maternal injection. Note arrows pointing to RBC's. D) Adult kidney 5 d post ip injection TAT-mMDH-eGFP. E) Adult kidney 5 post ip injection TAT-GFP.

FIG. 8: Construction of TAT-mMDH-eGFP Fusion Protein. The pTAT-HA vector contains a multiple cloning site (MCS) flanked by a termination codon (Term) and hemagglutinin (HA) tag for antibody detection. The sequence of the TAT peptide is displayed in red (SEQ ID NO:9) and is preceded by a His tag for nickel affinity purification. The cDNA for enhanced Green Fluorescent Protein (eGFP) was subcloned into the NCO I restriction site in frame with the mMDH transit peptide, expressed in E. coil, purified using nickel affinity chromatography, and denatured with urea and ion exchange chromatography prior to use.

FIG. 9: PET Scan of mouse heart. An adult mouse was injected with 1 mCi [$^{18}$F]2-fluoro-2-deoxy-D-glucose (FDG). Images were taken 1 hour after tail vein injection. Static images taken over 20 min show very good detail of cardiac uptake of labeled glucose. Images gated for heart rate based on the electrocardiogram, and crosshairs are centered on the heart. This figure shows the feasibility and resolution of the MicroPET for imaging the mouse. Right (R), Left (L), Dorsal (D), Ventral (V).

FIG. 10: Construction of TAT-mMDH-eGFP Fusion Protein. The pTAT-HA vector contains a multiple cloning site (MCS) flanked by a termination codon (Term) and hemagglutinin (HA) tag for antibody detection. The sequence of the TAT peptide is displayed in red (SEQ ID NO:9) and is preceded by a His tag for nickel affinity purification. The cDNA for enhanced Green Fluorescent Protein (eGFP) was subcloned into the NCO I restriction site in frame with the mMDH transit peptide, expressed in *E. coli*, purified using nickel affinity chromatography, and denatured with urea and ion exchange chromatography prior to use.

FIG. 11: TAT-fusion protein transduction causes phosphatidylserine flip. In FIG. 11, starting with B (A not shown), phosphatidylserine (PS) flip is detected by Annexin-V staining in cell culture. Cells were treated for 12 hours with 300 µM $H_2O_2$ and stained with Annexin-V (B) As a control untreated cells were also stained with Annexin-V (C). Cells were incubated with 0.01 mg.ml TAT-GFP and stained with Annexin V (D,E). Cells were also pretreated with polylysine prior to incubation with TAT-GFP and Annexin-V staining (F) Fluorescent levels of activated Caspase3were measured in cultured cells that were treated with either 0.01 mg/ml (29.5 µM) TAT-GFP (diagonal bars) or hydrogen peroxide for 12 hours (solid black bars) (G)

FIG. 12. Transduction of human Frataxin into NIH 3T3 cells. Analysis by confocal microscopy shows the TAT-Frataxin fusion protein transduces into NIH-3T3 cells. Cells were stained with CMX-Rosamine alone (A). A DIC image shows cell structure (B). Cells were incubated with human Frataxin fusion protein and labeled with fluorescene (bright green color) (C). Staining shows co-localization of CMX-Rosamine and human Frataxin within mitochondria (D).

DETAILED DESCRIPTION OF THE PREFERRED EMBODIMENTS

The disclosures of all United States Patent references cited herein are to be incorporated by reference herein in their entirety.

Compounds or conjugates of the present invention are prepared from three components: (a) a mitochondrial membrane-permeant peptide; (b) a compound of interest such as a detectable group or compound, an active mitochondrial protein or peptide, nucleic acids, drug or signaling agent,; and (c) a mitochondrial targeting sequence.

Mitochondrial membrane-permeant peptides that may be used to carry out the present invention. While any suitable peptide may be used, preferred peptides are HIV-TAT peptides. For example, the Tat peptide can comprise any sequential residues of the Tat protein basic peptide motif 37-72 (Vives et al. 1997) (37-CFITKALGISYGRKKRRQRRRP-PQGSQTHQVSLSKQ-72 (SEQ ID NO:1). The minimum number of amino acid residues can be in the range of from about three to about six, preferably from about three to about five, and most preferably about four, i.e., the minimal requirement for one alpha helical turn. One embodiment comprises Tat protein residues 48-57 (GRKKRRQRRR) (SEQ ID NO:2). See, e.g., U.S. Pat. No. 6,348,185 to Piwnica-Worms. Additional mitochondrial permeant peptide transduction domains comprise the sequences listed in Table 1.

TABLE I

Protein Transduction Domains

| PTD Name | Sequence | Notes | Ref. |
|---|---|---|---|
| TAT | YGRKKRRQRRR (SEQ ID NO:3) | HIV DNA binding domain | S. Schwarze, et al., Science 285:1569-1572 (1999). |
| PTD-4 | YARAAARQARA (SEQ ID NO:4) | 33x more efficient than TAT | A. Ho, et al., Cancer Research 61:474-477 (2001). |
| Pep-1 | KETWWETWWTEWS QPKKKRKV (SEQ ID NO:5) | 3 domains. Does not require cross-linking to transduced protein | M. Morris, et al., Nature Biotechnology 19:1173-1176 (2001). |
| Transportan | GWTLNSAGYLLGKIN LKALAALAKKIL (SEQ ID NO:6) | Neuropeptide of galanin (1-13) and mastoparan (14-27) | M. Pooga, et al., FASEB Journal 12:67-77 (1998). |
| Antennapedia | RQIKIWFQNRRMKW KK (SEQ ID NO:7) | DNA binding domain | D. Derossi, et al., Journal of Biological Chemistry 271:18188-18193 (1996); G. Pietersz, et al., Vaccine 19:1397-1405 (2001). |
| VP22 | DAATATRGRSAASRP TERPRAPARSASRPR RPVE (SEQ ID NO:8) | HSV-1 tegument protein | G. Elliott, and P. O'Hare, Cell 88:223-233 (1997); W. Derer, et al., FASEB Journal 16:132-133 (2002). |
| Cre | Cre Recombinase, ~41 kDa. | DNA binding protein from Cre recombinase | E. Will, et al., Nucleic Acids Research 30(12):e59 (2002) |
| $R_7$, $R_9$, $r_9$ | Oligomers of D- and L-arginine | D-Arg ($r_9$) 100-fold >TAT uptake rate | J. Rothbard, et al., Journal of Medicinal Chemistry 45:3612-3618 (2002); L. Chen, et al., Chemistry & Biology 8:1123-1129 (2001); P. Wender, et al., Proceedings of the National Academy of Sciences of the United States of America 97:13003-13008 (2000) |

Compounds of interest that may be used to carry out the present invention are proteins or peptides that have activity in the mitochondrial for any purpose, including diagnostic, therapeutic, and histological purposes. In one embodiment of the invention, the active mitochondrial protein or peptide is Frataxin; in another embodiment, the mitochondrial protein or peptide is trifunctional protein alpha. The active mitochondrial proteins or peptides are preferably mammalian in origin, and most preferably human in origin.

Mitochondrial targeting sequences that may be used to carry out the present invention include any sequence that is cleaved within the mitochondrial matrix, but not cleaved within the cellular cytoplasm, of a target cell into which the compound is delivered. Particular examples include the mitochondrial malate dehydrogenase cleavage sequence and mitochondrial creatine kinase (MtCK) sequence. The targeting sequence may be one that is not ordinarily found associated with the active protein or peptide (that is, a heterologous sequence), or may be one that is native to the active protein or peptide as found in the Frataxin and tri-functional proteins or peptides (TFP) (that is, a homologous sequence).

Compounds of the present invention can be prepared and formulated from the above in accordance with techniques known in the art, including but not limited to those described in U.S. Pat. No. 6,348,185 to Piwnica-Worms.

Subjects to be treated by the compounds and methods described herein include both human subjects and animal subjects (particularly mammalian subjects such as mice, cats, dogs, etc.) for medical, veterinary, and drug development purposes. The subject, including human subjects, may be male or female, and may be at any stage of development, including neonate, infant, child, adolescent, adult and geriatric subjects. Cells or tissues used to carry out the present invention include those from like subjects, such as muscle, nerve, and liver cells and tissues.

Compounds for conjugation with mitochondrial membrane-permeant peptides. An active compound, active agent or compound of interest of the present invention may be any suitable compound and includes, but is not limited to, peptides, proteins, enzymes (both protein and non-protein), nucleic acids, oligonucleotides, lipids, phospholipids, steroids, metal chelators, free radical scavengers, vitamins, drugs and prodrugs. The active agent may be active for any purpose and thus may be a therapeutic agent, a diagnostic agent, an imaging/staining agent, etc.

In some embodiments the active agent is a detectable group, e.g., a fluorescent group such as green fluorescent protein, a luminescent group, a spin label, a photosensitizer group for singlet oxygen generation, a photocleavable moiety, a chelating center, a heavy atom, a radioactive isotope, an isotope detectable by nuclear magnetic resonance, a paramagnetic atom (see, e.g., U.S. Pat. Nos. 6,686,458; 6,294,340; 6,251,584; etc.).

Conjugates. The mitochondrial-permeant peptides of this invention can be conjugated to an array of active compounds as described above. Conjugation may be direct or indirect (e.g., through an intermediate molecule or binding pair) and may be covalent or noncovalent. The conjugations can be carried out using any suitable method, including but not limited to those described below.

Peptides/proteins conjugated to other peptides/proteins. If both components are peptides or proteins then the conjugation may be carried out by recombinant methods [EP388 758 (referenced by Curiel et al in U.S. Pat. No. 6,274,322); Sambrook et al., Molecular Cloning: A Laboratory Manual (2d ed. 1989)); U.S. Pat. No. 6,803,053].

Peptides/proteins conjugated to nucleic acids. (1) The conjugation of peptides or proteins to nucleic acids can be done using the methods of Curiel et al. in which substances having an affinity for nucleic acids are bound to the proteins or peptides, (U.S. Pat. Nos. 5,521,291; 6,274,322; [also 6,077,663; 5,354,844; 5,792,645; 5,547,932; 5,981,273; 6,022,735; the disclosures of which are fully incorporated by reference herein). Substances with an affinity for nucleic acid which may be used include, for example, homologous polycations such as polylysine, polyarginine, polyornithine or heterologous polycations having two or more different positively charged amino acids, these polycations possibly having different chain lengths, and also non-peptidic synthetic polycations such as polyethyleneimine. Other substances with an affinity for nucleic acid which are suitable are natural DNA-binding proteins of a polycationic nature such as histones or protamines or analogues or fragments thereof.

The coupling of the peptide or protein with the polycation may be carried out by means of disulphide bridges, which can be cleaved again under reducing conditions (e.g. when using succinimidyl-pyridyldithiopropionate; by means of compounds which are substantially stable under biological conditions (e.g. thioethers by reacting maleimido linkers with sulfhydryl groups of the linker bound to the second component) or by bridges which are unstable under biological conditions, e.g. ester bonds, or acetal or ketal bonds which are unstable under slightly acidic conditions.

Furthermore, the binding of peptides or proteins to a substance having an affinity for nucleic acids such as polyamine can be carried out by means of transglutaminase. Transglutaminases comprise a number of different enzymes which catalyze the formation of epsilon-(gamma-glutamyl)lysine bonds in the presence of $Ca^{++}$ and with cleaving of $NH_3$.

Additional methods of preparing the polycation conjugates include: coupling the peptide or protein to the polycation via a biotin-protein bridge using streptavidin or avidin. The streptavidin or avidin is then chemically conjugated to polylysine in a similar manner to the product of transferrin-polylysine conjugates. Binding between proteins and polylysine may also be achieved by coupling polylysine with a lectin which has an affinity for a glycoprotein, the bonding in such a conjugate being effected by means of the bond between the lectin and the glycoproteins.

(2) A further method of binding target molecules to nucleic acids is called Systematic Evolution of Ligands by Exponential Enrichment, termed SELEX, is described in U.S. Pat. No. 5,475,096 entitled "Nucleic Acid Ligands," and U.S. Pat. No. 5,270,163 entitled "Methods for Identifying Nucleic Acid Ligands," both of which are specifically incorporated by reference herein. The SELEX process provides a class of products referred to as nucleic acid ligands, each ligand having a unique sequence and property of binding specifically to a desired target compound or molecule. The SELEX method includes steps of: (1) contacting the mixture with the target under conditions favorable for binding, (2) partitioning unbound nucleic acids from those nucleic acids which have bound specifically to target molecules, (3) dissociating the nucleic acid-target complexes, (4) amplifying the nucleic acids dissociated from the nucleic acid-target complexes to yield a ligand-enriched mixture of nucleic acids, (5) then reiterating the steps of binding, partitioning, dissociating and amplifying through as many cycles as desired to yield highly specific high affinity nucleic acid ligands to the target molecule. U.S. Pat. No. 6,737,236

Furthermore, the basic SELEX method has been modified. For example, SELEX based methods for selecting nucleic acid ligands containing photoreactive groups capable of binding and/or photocrosslinking a target molecule, including a protein or peptide, have been described (U.S. Pat. Nos. 5,763, 177, 6,001,577, 6,730,482). Methods that modify nucleotides and confer improved characteristics on the ligand, such as improved in vivo stability or improved delivery characteristics including chemical substitutions at the ribose and/or phosphate and/or base positions, are also described (U.S. Pat. No. 5,660,985, U.S. patent application Ser. No. 09/134,028, d, U.S. patent application Ser. No. 08/264,029).

A method for the synthesis of oligodeoxynucleotides terminated by 5'-amino-5'-deoxythymidine has been described (Bruick et al. (1997) Nucleic Acids Res. 25:1309-1310. This method uses a DNA template to direct the ligation of a peptide to an oligonucleotide, in which the peptide is presented by a second oligonucleotide in the form of a reactive thioester-linked intermediate.

Peptides/proteins conjugated to other macromolecules. (1) Cycloaddition reactions, including Diehls-Alder reactions, 1,3-dipolar cycloaddition reactions and [2+2] cycloaddition reactions, as described in U.S. Pat. No. 6,737,236; which is specifically incorporated by reference herein, provide a chemoselective and highly efficient method for derivatizing or conjugating macromolecules with other molecular entities. This method describes conjugation of peptides with such molecular entities as oligonucleotides, nucleic acids, proteins, peptides carbohydrates, polysaccharides, glycoproteins, lipids, hormones, drugs or prodrugs. Accordingly, a macromolecule bearing a moiety capable of undergoing a cycloaddition reaction, is reacted with another molecular entity bearing a moiety capable of undergoing a cycloaddition reaction with the moiety attached to the macromolecule to yield via a cycloaddition reaction efficient conjugation of the molecular entity to the macromolecule. More specifically, a macromolecule bearing either a diene or dienophile moiety is reacted with another molecular entity bearing either a dienophile or a diene moiety, respectively, to yield via a cycloaddition reaction efficient conjugation of the molecular entity to the macromolecule. The Diels-Alder reaction, in particular, is an ideal method for covalently linking large water soluble macromolecules with other compounds as the reaction rate is accelerated in water and can be run at neutral pH. (Rideout and Breslow (1980) J. Am. Chem. Soc. 102:7816). Additionally, the nature of the reaction allows post-synthetic modification of the hydrophilic macromolecule without excess reagent or hydrolysis of the reagent (U.S. Pat. No. 6,737,236).

The method of cycloaddition reactions can be extended to the conjugation of any macromolecule with another molecular entity with the macromolecule or molecular entity including but not limited to oligonucleotides, nucleic acids, proteins, peptides carbohydrates, polysaccharides, glycoproteins, lipids, hormones, drugs or prodrugs. For example, a peptide or protein that contains an amino acid building block which has been derivatized with a diene or dienophile, such as O-3,5-hexadiene-tyrosine or serine, or N-maleimidolysine, can be conjugated to another molecular entity including, but not limited to, another peptide, an oligonucleotide, nucleic acid, carbohydrate, detector molecule etc. without limitation. Natural macromolecules such as proteins can be derivatized with a diene or dienophile bearing heterobifunctional crosslinking reagent, such as the NHS ester of 3-(4-maleimidophenyl)-propionic acid, which allows subsequent conjugation to a macromolecule or diagnostic detector molecule bearing a corresponding diene or dienophile group, (U.S. Pat. No. 6,737,236).

(2) Finally, bioconjugates can be made according to the method of U.S. Pat. No. 6,790,827, entitled "Bioconjugation of Macromolecules," which describes the method of creating bioconjugates between a bioactive agent and an organocobalt complex and is specifically incorporated by reference herein. In this method the bioactive agent is covalently bonded directly or indirectly (via a spacer—polymethylene, ester, carbonate, ether, acetal or any combination of two or more of these units) to the cobalt atom of the organocobalt complex. The organocobalt complex binds the bioactive agent covalently to the cobalt such that the cobalt-bioactive agent bond is readily cleavable.

For this method the bioactive agent is any biologically active molecule that can form a conjugate with an organocobalt complex. The bioactive agent includes but is not limited to, peptides, oligopeptides, proteins, apoproteins, glycoproteins, antigens and antibodies or antibody fragments, protein analogs in which at least one non-peptide linkage replaces a peptide linkage, enzymes, coenzymes, enzyme inhibitors, amino acids and their derivatives, hormones, lipids, phospholipids, vitamins, minerals and nutritional additives, nucleotides, oligonucleotides, polynucleotides, and their art-recognized and biologically functional analogs and derivatives, plasmids, cosmids, artificial chromosomes, etc.

The organocobalt complex is any organic complex containing a cobalt atom having bound thereto 4-5 nitrogen and/or chalcogens such as oxygen, sulfur, etc., as part of a multiple unsaturated heterocyclic ring system. Suitable organocobalt complexes include, but are not limited to, cobalamin (coenzyme $B_{12}$), Co[SALEN] (which is a cobalamin analogue), organo(pyridine)-bis(dimethylglyoximato)cobalt, corrinoids and derivatives or analogues of any of the preceding, as well as pharmaceutically acceptable salts. The organocobalt complexes may be unsubstituted or substituted with conventional organic functional groups that will not alter the basic nature of the organocobalt complex, (U.S. Pat. No. 6,790,827).

Substituents which may be found on the organocobalt complex include amino, nitro, halogen (bromine, chlorine), sulfito, $C_{2-6}$-alkene and $C_{2-6}$ alkyne. For example, the organocobalt complex can be formed having a nitro and/or halo (e.g., bromo) derivative of the corrin ring or having an extended conjugation with exocyclic olefin or alkylene groups. Other derivatives include cobalamin lactone, cobalamin lactame and those in which the benzimidiazole ring (e.g., of cobalamin, green corrinoid, and the like) are substituted with e.g., one or more halogen (bromine, chlorine), hydroxy or $C_{1-6}$ alkyl. Further derivatives include anilide, ethylamide, mono-, di- or tri-carboxylic acid or proprionamide derivatives of cobalamin of Vitamin $B_{12}$.

Background on Human Mitochondrial Trifunctional Protein Deficiency. Mitochondria primarily utilize two different fuels for the generation of oxidative energy: pyruvate, derived from cytosolic glycolysis of glucose, and fatty acids which enter the β-oxidative pathway. Glucose is the major fuel for brain which cannot utilize fatty acids. It can, however, readily oxidize the ketone bodies derived from acetyl CoA and acetoacetyl CoA produced from β-oxidation in the liver. Fatty acid oxidation is a multi-step pathway that generates more than six times the energy of an equivalent mass of hydrated glycogen. Thus, fatty acid oxidation is the major source of energy for many tissues such as heart and skeletal muscle, where high density of energy is important. Fuel sources change dramatically around the time of birth in humans. While glucose is the predominant fuel for the fetus, after birth, fats derived from milk become more important in metabolism. Thus, defects in fatty acid metabolism frequently manifest themselves in the first year of life, in part, because of this switch.

Both pyruvate (from glycolysis) and fatty acids are selectively transported into the mitochondrial matrix where they are converted to acetyl CoA and enter the tricarboxylic acid cycle (TCA). The conversion of fatty acids to acetyl CoA in the β-oxidation spiral occurs via the repetitive step-wise removal of two carbon units from the carboxyl end of fatty acid molecules producing one molecule of acetyl CoA, and one molecule each of $FADH_2$ and NADH (FIG. 1) (D. Kelly, and A. Strauss, *New England Journal of Medicine* 330:913-919(1994)). The first reaction of the four enzymatic steps in the β-oxidation spiral is catalyzed by the acyl-CoA dehydrogenases, which are a family of enzymes with overlapping substrate specificity. These consist of a short chain acyl-CoA dehydrogenase (SCAD), a medium chain acyl-CoA dehydrogenase (MCAD), a long chain acyl-CoA dehydrogenase (LCAD) and a very long chain acyl-CoA dehydrogenase (VLCAD). The last three reactions of the fatty acid β-oxidation spiral for longer chain substrates are catalyzed by the mitochondrial trifunctional protein (TFP) which consists of the long chain enoyl-CoA hydratase, the long chain 3-hydroxyacyl-CoA dehydrogenase (LCHAD), and the long chain 3-ketoacyl-CoA thiolase. The TFP complex is a heterocomplex composed of four α and four β chains associated with the inner mitochondrial membrane (Y. Uchida, et al., *Journal of Biological Chemistry* 267:1034-1041(1992)). The carboxy-terminal domain of the α-chain (TFPα) contains the LCHAD activity that catalyzes the $3^{rd}$ step of the β-oxidation spiral. The N-terminal domain of TFPα contains the long chain 3-enoyl-CoA hydratase activity that catalyzes the $2^{nd}$ step. The β-chain (TFPβ) contains the long chain 3-ketoacyl-CoA thiolase activity and catalyzes the $4^{th}$ step in the β-oxidation spiral.

Defects in fatty acid oxidation are among the most common of inherited recessive metabolic disorders with an estimated incidence in the population of ~1 in 12,000 (J. Wood, et al., *Pediatrics* 108:E19 (2001)). These defects can present with a Reye-like syndrome in children including encephalopathy, hypoglycemia, and metabolic derangements that can lead to death. Of these, defects in medium chain acyl-Coenzyme A (CoA) dehydrogenase are the most common with a prevalence of 1 in 10,000 to 1 in 15,000 live births and can have a mortality as high as 25% (K. Tanaka, et al., *Human Mutation* 1:271-279 (1992); C. Wilson, et al., *Archives of Disease in Childhood* 80:459-462 (1999)). Defects may also occur in the TFP which represents 3 of the 4 enzymatic steps for degradation of fatty acids to fuel mitochondria. These defects fall into two biochemical subgroups (S. Ushikubo, et al., *American Journal of Human Genetics* 58:979-988, 1996; J. Ibdah, et al., *Journal of Clinical Investigation* 102:1193-1199(1998); J. Brackett, et al., *Journal of Clinical Investigation* 95:2076-2082 (1995); S. Jackson, et al., *Journal of Clinical Investigation* 90:1219-1225 (1992)). The first group has isolated LCHAD deficiency but normal or slightly reduced hydratase and thiolase activities. The second group has complete TFP deficiency. In children, these present most often as a deficiency in LCHAD. Children with LCHAD deficiency may present at a few months of age with an acute metabolic crises consisting of low blood sugar (hypoglycemia) and hepatic encephalopathy that can progress rapidly to death. These episodes frequently follow a prolonged period of fasting or stress, such as might be experienced during the flu with vomiting and diarrhea. Other manifestations of LCHAD deficiency may include cardiomyopathy, muscle weakness, or sudden infant death syndrome (R. Pollitt, *Journal of Inherited Metabolic Disease* 18:473-490 (1995)).

An interesting finding has been that most heterozygous women who carried LCHAD deficient fetuses frequently develop serious, and life-threatening metabolic disorders such as acute fatty liver of pregnancy (AFLP) or the syndrome of hemolysis, elevated liver enzymes, and low platelets (HELLP syndrome) (J. Ibdah, et al., *Molecular Genetics & Metabolism* 71:182-189 (2000)). The development of AFLP is devastating with high neonatal and maternal morbidity and mortality and recent data strongly suggests that the block at LCHAD in the fetus or placenta causes accumulation of long-chain 3-hydroxyacyl metabolites in the mother that are highly toxic to the liver (J. Ibdah, et al., *New England Journal of Medicine* 340:1723-1731(1999)). Supporting this hypothesis is the observation that this effect on the mother is not seen in infants completely deficient in TFP. The prevalence of AFLP is high at 1 in 7,000 to 1 in 13,000 deliveries and expectant mothers will develop hepatic failure with encephalopathy in the $3^{rd}$ trimester if not diagnosed and delivery quickly accomplished (C. Riely, *Seminars in Liver Disease* 7:47-54 (1987); T. Knox, and L. Olans, *New England Journal of Medicine* 335:569-576 (1996); M. Castro, et al., *American Journal of Obstetrics & Gynecology* 174:211-216 (1996)).

Background on the Mitochondrial Trifunctional Protein Animal Model. An animal model of the human TFP deficiency has been generated (J. Ibdah, et al., *Journal of Clinical Investigation* 107:1403 -1409 (2001)). Biochemical and histologic abnormalities of the homozygous animals closely approximates that of TFP deficiency in the human (R. Wanders, et al.; *Journal of Inherited Metabolic Disease* 22:442-487 (1999)).

Pharmaceutically Acceptable Salts of Peptide Complexes. Like amino acids, peptides and proteins are ampholytes, i.e., they act as both acids and bases by virtue of the presence of various electron-donor and acceptor moieties within the molecule. The peptide complexes of the present invention can therefore be used in the free acid/base form, in the form of pharmaceutically acceptable salts, or mixtures thereof, as is known in the art. Such salts can be formed, for example, with organic anions, organic cations, halides, alkaline metals, etc.

The term "pharmaceutically acceptable salts" embraces salts commonly used to form alkali metal salts and addition salts of free acids or free bases. The nature of the salt is not critical, provided that it is pharmaceutically acceptable. Suitable pharmaceutically acceptable base addition salts of the present peptide complexes include metallic salts and organic salts.

Preferred metallic salts include, but are not limited to, appropriate alkali metal (group Ia) salts, alkaline earth metal (group IIa) salts, and other physiologically acceptable metals. Such salts can be prepared, for example, from aluminum, calcium, lithium, magnesium, potassium, sodium, and zinc.

Organic salts can be prepared from tertiary amines and quaternary ammonium salts, including in part, tromethamine, diethylamine, N,N'-dibenzyl-ethylenediamine, chloroprocaine, choline, diethanolamine, ethylenediamine, meglumine (N-methyl-glucamine), and procaine.

Such salts can also be derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate, and undecanoate.

The basic nitrogen-containing groups can be quaternized with agents such as lower alkyl halides, such as methyl, ethyl, propyl, and butyl chloride, bromides, and iodides; dialkyl sulfates such as dimethyl, diethyl, dibuytl, and diamyl sulfates; long chain halides such as decyl, lauryl, myristyl, and stearyl chlorides, bromides, and iodides; aralkyl halides such as benzyl and phenethyl bromides, and others.

All of these salts can be prepared by conventional means from the corresponding peptide complex disclosed herein by reacting the appropriate acid or base therewith. Water- or oil-soluble or dispersible products are thereby obtained as desired.

Formulations/Pharmaceutical Compositions. The compounds of the present invention can be formulated as pharmaceutical compositions. Such compositions can be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Suppositories for rectal administration of the compounds discussed herein can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

Solid dosage forms for oral administration may include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form will vary depending upon the patient and the particular mode of administration.

Doses/Quantities of Peptide Complexes. The amount of complex comprising a drug or other pharmacologically active agent for administration to a patient to treat or prevent a disease condition will vary with the type of drug, and will comprise a therapeutically effective amount thereof. Drug dosages for treating various conditions are well known in the art. Note in this regard, for example, Goodman & Gilman's The Pharmacological Basis of Therapeutics, 1996, Ninth Edition, McGraw-Hill, New York.

Routes of Administration. The complexes of the present invention can be administered by a variety of methods, including, for example, orally, enterally, mucosally, percutaneously, or parenterally. Parenteral administration is preferred, especially by intravenous, intramuscular, subcutaneous, intracutaneous, intraarticular, intrathecal, and intraperitoneal infusion or injection, including continuous infusions or intermittent infusions with pumps available to those skilled in the art. Alternatively, the complexes can be administered by means of micro-encapsulated preparations, for example those based on liposomes as described in European Patent Application 0 213 523.

Treatment Regimens and Methods of Treatment. The regimen for treating a patient with the compounds and/or compositions of the present invention is selected in accordance with a variety of factors, including the age, weight, sex, diet, and medical condition of the patient, the severity of the condition, the route of administration, pharmacological considerations such as the activity, efficacy, pharmacokinetic, and toxicology profiles of the particular pharmacologically active compounds employed.

Administration of the drug complexes disclosed herein should generally be continued over a period of several days, weeks, months, or years. Patients undergoing treatment with the drug complexes disclosed herein can be routinely monitored to determine the effectiveness of therapy for the particular disease or condition in question.

Continuous analysis of the data obtained by these methods permits modification of the treatment regimen during therapy so that optimal amounts of the pharmacologically active substance in the peptide complex are administered, and so that the duration of treatment can be determined as well. Thus, the treatment regimen/dosing schedule can be rationally modified over the course of therapy so that the lowest amounts of drug compound is administered, and so that administration of such compounds is continued only so long as is necessary to successfully treat the disease or condition. In general, the dosage may be from about 0.001, 0.01, 0.05, 0.1 or 0.5 to about 10, 50, 100, 500 or 1000 mg/kg, with dosages of about 0.05 to about 500 mg/kg preferred, and dosages of about 0.5 to about 5 mg/kg most preferred, depending upon the particular disease, condition of the subject, route of administration, compound formulation, etc.

Disorders or diseases that may be treated by the methods of the present invention are, in general, mitochondrial disorders, particularly nuclear and mitochondrial genome disorders such as Friedreich's ataxia, human mitochondrial trifunctional protein deficiency, sudden infant death syndrome, Kearns-Sayre syndrome, and Leber's Hereditary Optic Neuropathy.

In some embodiments, useful for the diagnosis of mitochondrial diseases in mammalian, particularly human, subjects, the compound of interest is a detectable group. The conjugate containing the detectable group can be contacted to cells or tissues, typically mammalian cells or tissues such as muscle cells or tissues, by any suitable technique in vivo or in vitro, for example by techniques conventional in the field of histology. The cells or tissues can be mounted, washed, and examined for the presence of the detectable group, e.g., by microscopy, with mitochondrial disease being indicated by an abnormal increase, abnormal decrease, abnormal distribution, or abnormal formation of mitochondria (e.g., accumulation of excessive mitochondrial in the subsarcolemma region) as compared to cells or tissues from a subject free of mitochondrial disease. Note that mitochondria can currently be detected only using histologic stains and techniques. Thus, only fixed tissues can be examined by light microscope or by electron microscope for mitochondrial defects such as Leber's Hereditary Optic Neuropathy. However, using the strategy of attaching a bioactive signaling compound, such as a metal ion (boron, for example) or a radiolabeled fatty acid (to be detected by PET scanning) to the compound or conjugate of the invention (e.g., TAT-mMDH-peptide) sequence, would allow investigation of active mitochondrial function in the living tissues. This is useful for following or monitoring recovery of tissues after disease, and allow better treatment of human disease. Also, the TAT-mMDH-peptide can be used to attach biotinylated groups which can then be localized within the mitochondria in living tissues. This is of great use when examining histological samples because it clearly identifies mitochondria that are healthy at the time of tissue harvest and fixation. Thus, the application and potential use of compounds or conjugates of the invention to detect active mitochondrial function in the living tissues and organs is great and will contribute to evaluation and management of patients in health and disease.

The present invention is explained in greater detail in the following non-limiting examples.

EXAMPLE 1

Trifunctional Protein Conjugates for the Treatment of Mitochondrial Trifunctional Protein Deficiency A. TAT-mMDH-eGFP A fusion protein was constructed using the TAT region from the HIV virus, a mitochondrial targeting leader peptide, and a reporter protein (green fluorescent protein, GFP) (FIG. 2A) (S. Schwarze, et al., *Science* 285:1569-1572 (1999)). A second fusion protein was constructed that included a mitochondrial targeting sequence (MTS), mitochondrial malate dehydrogenase (mMDH), within the TAT-fusion protein in addition to the mitochondrial targeting leader peptide and reporter protein. The transduction of TAT-mMDH-eGFP was compared to that of TAT-GFP (a TAT-fusion protein that does not contain a MTS) into isolated mitochondria, NIH 3T3, and differentiated PC12 cells in culture, and multiple tissues of adult and pregnant mice. These proteins transversed both the cell membrane and mitochondrial membranes, and crossed the placenta into the fetus as well. While the mechanism of the protein movement across cell membranes is not understood, it is clear that TAT-fusion proteins get into mitochondria because of the TAT-peptide and not because of the MTS. Furthermore, when a MTS is present (TAT-mMDH-eGFP) the fusion protein is retained within the mitochondria over time because of processing of the MTS by mitochondrial protease mechanisms. This is an important finding since the TAT-fusion protein follows a chemical gradient and easily transduces back out of the mitochondria or cell if it is not localized by processing or formation of a larger protein complex.

Recognition of the mMDH signal sequence and transduction of membranes in isolated mitochondria: To show that the mMDH signal peptide was recognized by the mitochondrial processing peptidases in the matrix, fresh rat liver mitochondria were isolated and shattered via sonication. The matrix contents were recovered and incubated with purified TAT-mMDH-eGFP (P. Grant, et al., *Nucleic Acids Research* 14:6053-6066 (1986); E. Sztul, et al., *Journal of Biological Chemistry* 263:12085-12091(1988)). The matrix signal peptidase progressively cleaved the mMDH signal sequence at two sites yielding two cleavage products of an estimated molecular mass of 32 kDa and 28.9 kDa (FIG. 2, A-C). FIG. 2D shows the resultant three bands representing the full length and the two cleavage products of the purified protein at the expected molecular masses.

To show that the TAT sequence can cross mitochondrial membranes, respiring mitochondria were isolated from rat liver and incubated with purified TAT-GFP and TAT-mMDH-eGFP protein for 15 minutes. All mitochondrial incubation reactions were then treated with Proteinase K to digest proteins that had not entered the mitochondrial matrix to ensure that the proteins on the SDS-PAGE, or western blot, only consisted of proteins inside mitochondria. Both TAT-GFP and TAT-mMDH-eGFP were found inside mitochondria as detected by anti-GFP antibody (FIG. 2E). Interestingly, TAT-mMDH-eGFP did not show processing (smaller MW on SDS-PAGE) after transduction into mitochondria. One explanation for this may be that the transduced protein is rapidly crossing the outer membrane and entering the intermembrane space but is much slower to cross the inner membrane into the matrix where the processing peptidases are located. TAT-fusion proteins may cross the inner membrane more slowly due to the higher protein content of the inner membrane.

TAT fusion proteins cross cell membranes: TAT-mMDH-eGFP and TAT-GFP fusion proteins transduced efficiently into cultured cells as shown by incubating purified protein with cultured NIH 3T3 cells. GFP activity was detected using confocal microscopy. In cells incubated with either TAT-GFP or TAT-mMDH-eGFP the signal was spread throughout the cells, although not within the nucleus, and at the same intensity for both fusion proteins (FIG. 3). As controls, cells were also incubated with recombinant GFP and mMDH-eGFP, both without a TAT sequence. No GFP signal was detectable within cells incubated with either protein (data not shown) demonstrating that the GFP signal found within cells and mitochondria is not due to endocytic uptake or simple diffusion but rather the presence of the TAT sequence.

TAT fusion proteins cross mitochondrial membranes in cultured cells: NIH 3T3 cells were co-incubated with purified fusion protein and CMX-Rosamine, a mitochondria-specific dye that is sequestered and fluoresces in mitochondria (N. Tarasova, et al., *J. Biol. Chem.* 272:14817-14824 (1997); M. Yasuda, et al., *J. Biol. Chem.* 273:12415-12421(1998); H. Wang, et al., *Cell* 87:629-638 (1996)), in order to demonstrate the presence of the GFP protein in mitochondria of cultured cells. The cells were viewed using a confocal microscope with two lasers set at different wavelengths; 488λ to detect the GFP signal from the TAT fusion protein and 543λ to detect the CMX-Rosamine signal from mitochondria. The images were superimposed to see overlapping areas of fluorescence. Both TAT-GFP and TAT-mMDH-eGFP were present in mitochondria shortly after exposure to the TAT-fusion proteins as shown by the yellow color from the overlapping images (FIG. 3).

GFP signal persists over time in TAT-mMDH-eGFP treated cells: TAT fusion proteins are reported to be dependent on concentration gradients (S. Schwarze, et al., *Science* 285: 1569-1572 (1999)). Removal of excess fusion protein from the surrounding media causes the TAT to diffuse out of the cells and their organelles. Purified fusion protein was incubated with cells to demonstrate that when the mMDH signal sequence is recognized and cleaved in the TAT-mMDH-eGFP construct, the TAT diffuses out of the mitochondria leaving behind the eGFP. Cultured NIH 3T3 or PC12 cells were incubated with purified fusion protein for 1 hour, after which the cells were washed, fresh medium added, and the cells placed back into the incubator for 1, 24, 48, or 72 hours. The cells were then incubated with CMX-Rosamine, and the images from both lasers overlapped as described above. Little to no GFP signal was detected in cells or mitochondria of TAT-GFP treated cells (FIG. 3). However, the GFP signal in TAT-mMDH-eGFP treated cells persisted up to 72 hours after initial incubation (FIG. 3). The GFP signal in these cells was primarily within mitochondria regardless of cell type.

The time course of TAT-GFP transduction into PC12 cells confirmed that this is a relatively fast process with signal being visible within 3 minutes of application (FIG. 4). Signal continues to increase over 20 minutes. The decreased rate of fluorescence change after 20 min may be accounted for by the time needed for TAT to organize and create a pore to allow efficient movement across the cell membrane.

GFP signal found in liver and heart mitochondria of mice injected with TAT-mMDH-eGFP: Mice were injected intraperitoneal (ip) with 2 mg/kg of either TAT-GFP or TAT-mMDH-eGFP and sacrificed either 17 hours later, or 5 days later. Liver, heart, kidney, and brain tissues were sectioned and examined under the confocal microscope (FIGS. 5 and 7). In addition, mitochondria and cytosolic fractions were isolated from the livers of the 5 day animals and separated by SDS-PAGE (25 µg total protein per lane) with transfer to nitrocellulose for staining with anti-GFP antibody (Molecular Probes) (FIG. 6). A strong GFP signal was detectable in heart and liver of TAT-mMDH-eGFP injected mice as detected at 17 hours (FIG. 5 A-C). GFP signal was present for the TAT-GFP mice (FIG. 5, D-E) though it was qualitatively not as strong as the TAT-mMDH-eGFP group. At 5 days after injection, however, the differences were much greater. Heart, and to a lesser extent, liver and brain, from animals injected with TAT-mMDH-eGFP had very strong signal (FIG. 5, G-I). Kidney, in particular, had a very strong signal after transduction of TAT-mMDH-eGFP at 5 days (FIG. 7D). In contrast, the animals injected with TAT-GFP had little signal visible in liver or brain, and moderate signal in heart (FIG. 5). There was almost no GFP signal in kidney from TAT-GFP at 5 days (FIG. 7E). FIG. 6 demonstrates that the entire TAT-mMDH-GFP signal in the 5 day animals is within the mitochondria and the transduced protein has been processed (smaller molecular weight). In the 5 day animals injected with TAT-GFP, all of the GFP is found in the cytosol with no GFP staining in mitochondria. These in vivo results are consistent with the in vitro cell culture results and show that cleavage of the mMDH signal sequence of TAT-mMDH-eGFP localized the eGFP protein within the mitochondrial matrix. The TAT-GFP was not cleaved and diffused out of the mitochondria, and out of the tissues.

TAT-fusion proteins cross the placenta. Pregnant mice at 18-19 days of gestation were injected intraperitoneally (ip) with 2 mg/kg of TAT-mMDH-eGFP. Sacrifice of the mother 24 hours later revealed extremely strong GFP in heart and served as a positive control (FIG. 7A). The fetus showed moderate GFP signal in heart at 24 hours after maternal injection indicating that the TAT-fusion protein easily crossed the placenta and entered the fetal circulation (FIG. 7B). A very strong GFP signal was present in heart from the 24 hour old pup indicating that TAT-mMDH-GFP had been processed and GFP remained within the mitochondria over time (FIG. 7C). Interestingly, the red blood cells (RBC's) were heavily stained in all tissues examined (arrows in FIG. 7C) suggesting that TAT-fusion proteins may concentrate in these cells. Pups from this experiment continued to show strong GFP fluorescence in heart and liver as far out as 7 days after maternal injection of TAT-mMDH-eGFP (data not shown). This suggests that the transduced protein may have a relatively long half-life in the mitochondria if the TAT peptide is removed.

The intensity and persistence of the GFP signal in TAT-mMDH-eGFP injected mice, as compared to TAT-GFP mice, correlated well with the persistence of GFP in the cell culture data. The strong GFP signal in TAT-mMDH-eGFP mice 5 days after injection is due to cleavage of the mMDH signal sequence within the mitochondria, otherwise it would not persist (FIGS. 5, 6, 7). Therefore, the intensity and persistence of the GFP signal, and processing of the MTS, signifies it is within mitochondria. These results illustrate that not only is this fusion protein able to deliver and localize a protein to mitochondria in vitro, but in vivo as well. Furthermore, these results show that the present invention, using TAT combined with a mitochondrial signal sequence is a feasible way to target and localize exogenous compounds to mitochondria.

Transduction of TAT-fusion proteins across the cell membrane causes phosphatidylserine flip. Transduction of TAT-fusion proteins across the cell membrane causes membrane phospholipids rearrangement as evidenced by a flip in the phosphatidylserine (PS) from inner to outer plasma membrane. TAT interacts with the negative charges on the phospholipids membrane to transduce. The PS flip is detected by Annexin-V staining in cell culture. Cells treated for 12 hours with 300 µM $H_2O_2$ stain positively with Annexin-V (FIG. 11B, while untreated cells do not have Annexin-V signal (FIG. 11C. Similarly, cells incubated with 0.01 mg.ml TAT-GFP also stain with Annexin V (FIG. 11D,E. However, pretreatment of cells with polylysine prior to incubation with TAT-GFP results in no Annexin-V signal nor is any TAT-GFP signal detected in the cell (FIG. 11F) In FIG. 11G fluorescent levels of activated Caspase-3 from cultured cells are shown after treatment with either 0.01 mg/ml (29.5 µM) TAT-GFP (diagonal bars) or hydrogen peroxide for 12 hours (solid black bars). Apoptosis is not initiated by this membrane rearrangement either in vivo or in vitro and thus, cell death is not expected in vivo.

B. Mitochondrial Trifunctional Protein Deficiency

TAT-fusion proteins offer a method of delivering biologically active proteins to correct or repair mitochondrial defects. However, two requirements must be met in order for this to occur: 1) The fusion protein must target only the mitochondria and remain located there. Non-specific targeting of a protein to a different organelle must be avoided because it may disrupt a vital process. 2) The fusion protein must achieve biological activity inside the mitochondria. The present invention meets both of these requirements.

Animal Model of Trifunctional Protein deficiency: TFPα deficient mice are maintained in the heterozygous state because the homozygous state is lethal to the neonatal animal. Specifically, the homozygous TFPα$^{-/-}$ animals develop fatty liver (lipidosis) quickly after birth, with degenerative changes in cardiac and diaphragmatic myocytes somewhat later. Affected homozygous animals die within 36 hours of birth.

Tissue culture and Isolation of Primary Hepatocytes: The pregnant mouse is killed by cervical dislocation at 19 days of gestation and the embryos removed using sterile technique. The embryos are washed in phosphate buffered saline (PBS) with antibiotics, transferred to a Petri dish with fresh PBS, and a piece of tail is cut for genotyping. The liver is dissected out, washed in PBS with antibiotics, minced and washed in PBS. The PBS is replaced with fresh PBS and antibiotics containing 0.25% trypsin (1 ml for 100 mg of tissue) and incubated at 4° C. for 6 to 18 hrs. The supernatant is then removed; the remaining tissue incubated at 36.5° C. for 30 minutes, and warmed tissue media (Ham's F12) with 10% fetal calf serum is added with gentle pipetting of the tissue until the cells are dispersed. Cell viability is determined using trypan blue and cells are plated at $1 \times 10^6$ cells per ml.

Primary and stable cell lines in culture are maintained in a 5% $CO_2$ atmosphere at 37° C. with media appropriate for the cell type, such as Dulbecco's Modification of Eagle's Medium (DMEM) with 5% bovine serum for NIH 3T3 cells. For transduction experiments with TAT-fusion proteins, the culture media is replaced with PBS for 15 minutes during which time the transduced protein is applied to the cells, the cells are then washed with PBS and the media is replaced.

TAT-fusion protein construction and purification: The cDNA to be expressed is subcloned in-frame into the vector containing the TAT amino acid sequence (FIG. 8) and when expressed has the TAT sequence at the N-terminus along with a 6xHis tag for purification on a nickel affinity (Ni-NTA) column. The purification strategy for these recombinant proteins includes a denaturing step with urea and shock denaturing on an ion exchange column following published methods (M. Becker-Hapak, et al., *Methods (Duluth)* 24:247-256 (2001)). The finished protein is quantified, sterile filtered, and frozen at −70° C. with 10% glycerol. The cDNA for mouse TFPα is cloned into the cloning site of the pTAT vector and, after sequencing the cDNA construct, the fusion protein is overexpressed in bacteria.

Isolation of mitochondria: Intact, respiring mitochondria are prepared from heart using limited tissue digestion with Nagarse (0.4 mg/ml) followed by tissue disruption with a Polytron at medium speed. The mitochondria are then isolated by differential centrifugation. Use of Nagarase results in recovery of virtually all intact mitochondria (D. Rickwood, et al., In *Mitochondria. A Practical Approach*. V. M. Darley-Usmar, Rickwood, D., and Wilson, M. T., editors. IRL Press Limited, Oxford, England. 1-16 (1987); E. Lesnefsky, et al., *American Journal of Physiology* 273: H1544-H1554 (1997)). Mitochondria isolated from rat liver following protocols well-known in the art, are used to ensure that all assays are working (D. Rickwood, et al., In *Mitochondria. A Practical Approach*. V. M. Darley-Usmar, Rickwood, D., and Wilson, M. T., editors. IRL Press Limited, Oxford, England. 1-16 (1987)).

Histology: Electron microscopy (EM) is used to examine cell ultrastructure and mitochondrial morphology ex vivo of liver and heart from treated, control, and untreated knock-out animals. Tissue is isolated from heart and liver and resuspended in fixative (4% glutaraldehyde, 100 mM sucrose, and 100 mM cacodylate buffer, pH 7.4), dehydration, and embedding for sectioning.

Tissue histology at the light microscope level is also used to evaluate hepatic, cardiac, and skeletal muscle responses to TAT-TFPα fusion protein rescue in the homozygous animal, and possible scar formation from defects in fatty acid oxidation in long-term follow-up (J. Fruchart, et al., *Current Opinion In Lipidology* 10:245-257 (1999)). Hematoxylin and eosin staining of cross sections from treated and control hearts and livers-provide data on phenotypic changes and tissue lipidosis. Oil Red O-stain is used on frozen sections to evaluate micro- and macrovesicular fatty infiltration. In addition, trichrome staining, or Azan-Mallory staining (K. Watanabe, et al., *Journal of Biological Chemistry* 275:22293-22299 (2000)) is used to determine the amount of scar tissue formation on long-term follow-up (4 weeks) after treatment. Images are scanned and digitized and the volume of scar tissue quantified.

Assessment of mitochondrial respiration: In order to follow the impact of fatty oxidation defects on mitochondrial injury. Mitochondrial respiration ratios will be determined using total mitochondria isolated from homozygous treated and untreated hearts and livers, and oxygen consumption measured with an oxygraph and Clark oxygen electrode (Yellow Spring Instruments, Yellow Spring, Ohio) (D. Rickwood, et al., In *Mitochondria. A Practical Approach*. V. M. Darley-Usmar, Rickwood, D., and Wilson, M. T., editors. IRL Press Limited, Oxford, England. 1-16 (1987)). Cultured myocytes are evaluated similarly (Z. Khuchua, et al., *Journal of Biological Chemistry* 273:22990-22996 (1998)). Oxygen consumption by heart mitochondria is measured in air saturated medium in a closed container with a magnetic stir bar at 28° C. A volume of 100 μL of the mitochondrial suspension is added to the respiration buffer which contains 0.3 M sucrose, 1 mM EGTA, 5 mM Mops, 5 mM $KH_2PO_4$, and 0.1% BSA at pH 7.4. Basal respiration ($V_o$) is recorded for 3 minutes, pyruvate and malate are added (final concentrations 5 mM and 2.5 mM, respectively), and state 3 respiration is stimulated by 60 μM ADP to submaximal level (VADP). State 4 respiration is measured after the ADP is depleted. Atractyloside, an inhibitor of the ATP-ADP translocator, is used to show this oxygen consumption is due to mitochondrial respiration. Oxygen consumption in rat liver mitochondria provides a second control to check the integrity of the system.

Determination of protein oxidation: Reactive oxygen species attack amino acid residues in proteins to produce carbonyl functional groups. Carbonyl formation is used as a marker for protein oxidation (P. Evans, et al., *Methods in Enzymology* 300:145-156 (1999); A. Reznick, and L. Packer, *Methods in Enzymology* 233:357-363 (1994)) using 2,4-dinitrophenylhydrazine (DNPH), which reacts with carbonyl groups to form protein hydrazones that are measurable spectrophotometrically. By obtaining the spectra at 355-390 nm, the concentration of hydrazones/ml can be calculated using Beer's Law: $C=A/\epsilon$, where A in the absorption and $\epsilon$ is the extinction coefficient. For DNPH, $\epsilon=45.45$ nmol/ml. Levels of manganese superoxide dismutase (MnSOD) mRNA are measured by slot blot analysis (Northern Blotting) using a cDNA probe for mouse MnSOD (Z. Chen, et al., *Journal of Molecular & Cellular Cardiology* 30:2281-2289 (1998)).

Biochemical Assays: Blood from animals for analysis is obtained by cardiac puncture at the time of sacrifice. Glucose, urea and bilirubin, alanine aminotransferase (ALT), and gamma glutamyl transferase (GGT) is measured by automated clinical analyzer on less than 1 cc of whole blood. Serum and tissue free fatty acids, serum acyl carnitine, and urine organic acids are analyzed using gas chromatography-mass spectrometry (R. Boles, et al., *Human Pathology* 25:735-741 (1994)). The activities of LCHAD and long chain 3-ketoacyl-CoA thiolase are measured on crude tissue extracts from heart and liver (R. Wanders, et al., *Biochemical & Biophysical Research Communications* 188:1139-1145 (1992)). Since the active site of these two enzymes are located in the α and β subunits of the TFP, a loss of activity in both is always associated with loss of the long chain 2,3 enoyl-CoA hydratase (TFPα chain). Gas chromatography-mass spectrometry is used to measure 3-hydoxy fatty acids in the cell culture media of TFPα deficient cells (P. Jones, et al., *Clinical Chemistry* 47:1190-1194 (2001)).

Positron Emission Tomography Scanning: Positron Emission Tomography (PET) Scanning is used to image cardiac and hepatic metabolism in TFPα deficient mice. Monitoring glucose and/or fatty acid uptake by the myocardium and liver in these animals using microPET allows evaluation and prediction of hepatic and myocardial fatty acid oxidation after treatment with TAT-fusion proteins (S. Bergmann, et al., *Journal of Inherited Metabolic Disease* 24:657-674 (2001)).

Animals are sedated with halothane and maintained on 1% halothane. The animals are monitored to ensure that they remain sedated for the length of the procedure and PET scan. At the conclusion of the PET study the animals are returned to their cages. PET imaging studies are performed prior to treatment with TAT-fusion proteins and redone after 1 week of TAT-fusion protein treatment to detect changes in fatty acid oxidation. The anesthetized animals are injected with 2.0 mCi of the radiotracer ($1$-$^{11}$C palmitate and $1$-$^{11}$C acetate) (S. Bergmann, et al., *Journal of Inherited Metabolic Disease* 24:657-674 (2001); S. Bergmann, et al., *Journal of Nuclear Medicine* 37:1723-1730 (1996)) via the tail vein. Palmitate is used to estimate long chain fatty acid consumption by mitochondria, and acetate estimates oxygen consumption by mitochondria (V. Davila-Roman, et al., *J.Am.Coll.Cardiol.* 40:271-277 (2002)). Immediately after injection the animals are placed in the microPET gantry, positioned via anterior and lateral lasers and imaged for 20 minutes over the torso to scan the heart and liver. Control mice are fasted for 12 hr. If there are difficulties injecting the radiotracer into the tail vein, the right internal jugular vein may be used for injection under direct visualization.

PET scans are performed on a Concorde Microsystems, Inc., microPET P4 PET scanner. This device has no septa and therefore operates exclusively in three-dimensional imaging mode with axial and transaxial fields of view of approximately 8 and 20 centimeters respectively. The reconstructed resolution is approximately two millimeters in all three axes. Data are reconstructed using three-dimensional filtered back-projection with a ramp filter cutoff at the Nyquist frequency (0.222 mm$^{-1}$).

All image processing following reconstruction uses region-of-interest (ROI) analysis. A spherical ROI is placed over the anatomical region of interest. The maximum and average value in the PET scan of the thresholded pixels within the ROI is recorded. Palmitate and acetate utilization are expressed using the differential uptake ratio (DUR) method (K. Kubota, et al., *Journal of Nuclear Medicine* 37:1713-1717 (1996)):

$$DUR = \frac{\text{counts/pixel}}{\text{Injection dose/rat body weight}}$$

Statistical Analysis: All values are presented as means±SD. For comparisons of responses between different groups, unpaired t-tests or analysis of variance are used. If the F-crit value is significant, then a pair-wise test (Student-Newman-Kuels) is performed. A $p<0.05$ is required in order to be significant.

The TAT peptide delivers an active mitochondrial protein in vitro. A mitochondrial targeting sequence is required for the matrix processing peptidases to recognize and cleave thereby fixing the protein in the matrix space. Without the targeting sequence, the TAT sequence remains attached and can facilitate diffusion of the TAT-fusion protein out of the matrix space, or inhibit normal folding and incorporation of the transduced protein into a biologically active complex. Prior to the present invention, this has not been accomplished for matrix proteins.

Protocol: The cDNA containing the coding sequence of mouse TFPα (GenBank Accession #XM131963) is subcloned into the TAT-vector. Prior to expression in *E. coli* the cDNA construct is sequenced to ensure that it is in frame. The A hemagglutinin (HA) tag is included for antibody detection. Nickel affinity chromatography is used for purification of the protein, and low-pressure chromatography for denaturation. TAT-TFPα protein purity and quantity are determined by gel electrophoresis.

The TAT-TFPα fusion protein is tested in cell culture to ensure it targets to the correct space in mitochondria and is proteolytically processed. This is done utilizing both antibody to TFPα and HA, and by fluorescent labeling (Molecular Probes) of synthetic protein prior to incubation with cells in culture. Processed protein is also isolated for use in sequencing by tandem MS-MS. The protein and mRNA levels of TFPβ are determined using antibodies and cDNA probes specific for this gene product (J. Ibdah, et al., *Journal of Clinical Investigation* 107:1403-1409 (2001)). Mitochondria are stained with CMX-H$_2$-Ros to check for integrity and co-localization with TFPα. The nuclei are counter-stained with Hoechst 33342 fluorescent marker to identify nuclear membranes. Initially NIH 3T3 cells are used because of their ease of manipulation and the high number of mitochondria that can be recovered from these cells. The fate of the TAT-HA-MTS when cleaved from the precursor TAT-TFPα fusion protein is determined by following its location and integrity using antibodies against the HA portion. The histology of the transduced cells will be examined at the light and EM levels, and mitochondrial respiration be measured on cells in culture as we have done for cultured myocytes (Z. Khuchua, et al., *Journal of Biological Chemistry* 273:22990-22996 (1998)). The appropriate controls include TFPα without the TAT sequence, and TAT-TFPα without the MTS (TAT-TFPα$^-$ $_{MTS}$). The use of TAT-mMDH-eGFP in parallel experiments ensures that the mitochondria have been targeted.

Rescue of the phenotype of an animal transgenic for the loss of TFP function. Biological activity of TAT-fusion proteins has been shown in vivo. However, until the present invention, transduction of biologically active fusion proteins into the mitochondrial matrix has not been shown. This is a crucial step in the repair of mitochondrial defects leading to human disease. This invention shows that the TAT-TFPα fusion protein can localize to the inner membrane of the mitochondrial matrix and integrate into a hetero-octamer of four α-subunits, and four β-subunits, to form an active TFP complex in vivo. In addition, since TFPβ is not stable and is rapidly degraded without TFPα, this invention shows that once the TAT-TFPα peptide is transduced into the mitochondria of a TFPα$^{-/-}$ mouse and processed then TFPβ is detectable.

Protocol: The effects of transduction of the TAT-TFPα fusion protein is shown in three experimental groups:
1. Control Group—wild type C57BL/6J mice at 3 to 4 months of age, as well as neonatal mice of the same strain. These animals express normal levels of TFP.
2. Neonatal TFPα$^{-/-}$ mice—neonatal mice homozygous for ablation of the TFPα gene. This is most easily determined by phenotype but is also be confirmed by Southern Blotting or PCR analysis (64).
3. Pregnant heterozygous females (TFPα$^{+/-}$)—pregnant dams heterozygous for the TFPα gene, bred with males heterozygous for the TFPα knockout state. Thus, 25% of the embryos will be homozygous TFPα$^{-/-}$ (knockout), 50% will be heterozygous TFPα$^{+/-}$, and 25% should be homozygous TFPα$^{+/+}$.

Following injection of the TAT-TFPα fusion protein into mice, proper delivery to the mitochondria in heart, liver, brain, and skeletal muscle is assayed for based on its biochemical activity, immunolocalization to mitochondria, and total protein mass. Impact of the transduced protein on the animal's growth and viability, and on tissue histology is determined using the above outlined protocol. TFP enzyme activity and other biochemical parameters are determined using the above outlined protocol. Positron Emission Tomography (micro-PET Scan) using [1-$^{11}$C]-palmitate and [1-$^{11}$C]-acetate as tracers is used to show that the rescued phenotype is able to utilize long-chain fatty acids for fuel.

The appropriate dosage and dosing intervals was determined using serial biochemical assays, TFPα and TFPβ protein mass, and physical condition in the homozygous TFPα$^{-/-}$ animals. This information was correlated with microPET scans of homozygous animals using labeled long chain fatty acids as tracers and compared with microPET scans from normal controls. Thus, yielding a non-invasive method for long-term tracking of mitochondrial function and functional recovery of TFP activity in the animal.

Distribution of the TAT-TFPα fusion protein in multiple tissues is shown by immunohistochemistry and Western blotting.

The immune response to chronic administration of TAT-Fusion proteins is studied to determine side effects of long-term administration of the protein. For this purpose enzyme-linked immunosorbent assays (ELISA) are performed on serum from animals injected for 1, 2, 4 and 12 months with TAT-fusion proteins (116). Inflammatory response is also examine in the control and homozygous knock-out animals for evidence of impaired mitochondrial respiration, and mitochondrial oxidative damage.

EXAMPLE 2

Frataxin Conjugates for the Treatment of Freidreich's Ataxia

Defects in mitochondrial function are common in human health and disease. Because mitochondria have only a small genome, ~16 kb, they must import most of the hundreds of proteins needed for their function from nuclear-encoded genes. Defects in these imported proteins are frequent causes of disease and metabolic disorders. Friedreich's Ataxia (FA) is one such disease and is the most common autosomal recessive ataxia. FA is caused by lack of the nuclear-encoded, mitochondrially targeted protein, Frataxin. FA is caused by a large expansion of a GAA triplet-repeat sequence in the first intron of the Frataxin gene leading to decreased transcription of full-length transcripts (elongation is inhibited) (P. Patel and G. Isaya, *Am. J. Hum. Genet.* 69:15-24 (2001)). The result being that Frataxin protein is severely deficient leading to progressive iron accumulation and dysfunction in mitochondria (O. Gakh, et al., *Biochemistry.* 41:6798-6804 (2002)). Patients with Friedreich's Ataxia present in childhood years with ataxia and limb weakness with progressive cardiomyopathy and motorneuron dysfunction and die in the 4$^{th}$ or 5$^{th}$ decade. Effective therapy for this progressive disorder has not been achieved.

Human Frataxin is translated as a ~29 kDa precursor protein with a 55 amino acid mitochondrial targeting sequence at the amino terminus. The precursor is processed in 2 steps to a smaller ~18 kDa mature peptide in the mitochondrial matrix that is then assembled into a homopolymer of ~1 MDa binding approximately 5 atoms of iron per molecule (P. Cavadini, et al., *Hum. Mol. Genet.* 11:217-227 (2002); P. Cavadini, et al., *J. Biol. Chem.* 275:41469-41475 (2000)).

Using the protein transduction domain, TAT, exogenous proteins can be delivered to mitochondria. Furthermore, by using a mitochondrial targeting sequence, the protein can be specifically targeted to mitochondria and processed leaving the mature protein within the mitochondrial matrix.

TAT-Frataxin fusion protein construct targets mitochondria. The cDNA for mouse Frataxin is subcloned in-frame behind the TAT peptide and expressed in *E. Coli*. The fusion protein is purified by affinity chromatography and purity determined by PAGE. Proper targeting is determined by incubation of precursor TAT-Frataxin with mitochondria to show proper processing and transduction into the matrix compartment. Transduction across both cell and mitochondrial membranes with localization in mitochondria is shown by application of TAT-Frataxin fusion protein to cells in culture.

The TAT-Frataxin fusion protein has been shown to transduce into NIH-3T3 cells (FIG. 12). NIH 3T3 cells were co-incubated with purified fusion protein and CMX-Rosamine, a mitochondria-specific dye that is sequestered and fluoresces in mitochondria (N. Tarasova, et al., *J. Biol. Chem.* 272: 14817-14824 (1997); M. Yasuda, et al., *J. Biol. Chem.* 273: 12415-12421(1998); H. Wang, et al., *Cell* 87:629-638 (1996)), in order to demonstrate the presence of the TAT-Frataxin in mitochondria of cultured cells (FIG. 12D). The cells were viewed using a confocal microscope and the images were superimposed to see overlapping areas of fluorescence. Successful transduction and sequestering of the human Frataxin into the mitochondria was observed.

The TAT-Frataxin Fusion Protein Rescues the FA Phenotype.

Animal Models of Frataxin Protein deficiency: The conditional knock-out mouse model of FA (FRDA deficiency) is available (H. Puccio, et al., *Nat. Genet.* 27:181-186 (2001)). Both a cardiac-specific, and a neuronal-specific knock-out have been generated although there is cross-over in the phenotypes. The homozygous FRDA knock-out is embryonic lethal (M. Cossee, et al., *Hum. Mol. Genet.* 9:1219-1226 (2000)).

Tissue culture and Isolation of Primary Cells: Primary and stable cell lines in culture are maintained in a 5% $CO_2$ atmosphere at 37° C. with media appropriate for the cell type, such as DMEM with 5% bovine serum for NIH 3T3 cells. For transduction experiments with TAT-fusion proteins, the culture media is replaced with PBS for 15 minutes during which time the transduced protein is applied to the cells, the cells are then washed with PBS and the media is replaced. Primary cells (fibroblasts) from FA patients or the knock-out mice, are grown in established conditions and the TAT-FA fusion protein transduced as outlined in the above protocols. Biochemical and histological protocols are outlined below.

TAT-fusion protein construction and purification: The cDNA for mouse Frataxin (precursor form: GenBank accession U95736) is subcloned in-frame into the cloning site of the pTAT vector. The cDNA construct is sequenced to ensued fidelity and that the Frataxin cDNA is in frame. Following sequencing the cDNA construct is overexpressed in bacteria. When expressed, the fusion protein has the TAT sequence at the N-terminus along with a 6×His tag for purification on a nickel affinity (Ni-NTA) column (FIG. 1 shows the strategy for construction of TAT-mMDH-GFP). The purification strategy for these recombinant proteins includes a denaturing step with urea and shock denaturing on an ion exchange column following published methods (M. Becker-Hapak, et al., *Methods (Duluth)* 24:247-256 (2001)). The purified protein is quantified, sterile filtered, and frozen at −70° C. with 10% glycerol. No mMDH targeting sequence is required because Frataxin has its own MTS. The adult and neonatal mice are injected in the peritoneum with 2 mg/kg body weight of the fusion protein. Cell culture media is prepared at a concentration of 0.01 mg/ml fusion protein.

Isolation of mitochondria: Intact, respiring mitochondria are prepared from heart using limited tissue digestion with Nagarse (0.4 mg/ml) followed by tissue disruption with a Polytron at medium speed. The mitochondria are then isolated by differential centrifugation. Use of Nagarase results in recovery of virtually all intact mitochondria (D. Rickwood, et al., In *Mitochondria. A Practical Approach*. V. M. Darley-Usmar, Rickwood, D., and Wilson, M. T., editors. IRL Press Limited, Oxford, England. 1-16 (1987); E. Lesnefsky, et al., *American Journal of Physiology* 273: H1544-H1554 (1997)). Mitochondria isolated from rat liver following protocols well-known in the art, are used to ensure that all assays are working (D. Rickwood, et al., In *Mitochondria. A Practical Approach*. V. M. Darley-Usmar, Rickwood, D., and Wilson, M. T., editors. IRL Press Limited, Oxford, England. 1-16 (1987)).

Histology: Electron microscopy (EM) is used to examine cell ultrastructure and mitochondrial morphology ex vivo of liver and heart from treated, control, and untreated knock-out animals. Tissue is isolated from heart and liver and resuspended in fixative (4% glutaraldehyde, 100 mM sucrose, and 100 mM cacodylate buffer, pH 7.4), dehydration, and embedding for sectioning.

Tissue histology at the light microscope level is used to evaluate hepatic, cardiac, and brain responses to TAT-Frataxin fusion protein rescue in the transgenic animal. Phenotypic changes are followed using hematoxylin and eosin staining of cross sections from treated and control hearts and brains with liver serving as a control. In addition, trichrome staining, or Azan-Mallory staining (K. Watanabe, et al., *Journal of Biological Chemistry* 275:22293-22299 (2000)) is used to determine the amount of scar tissue formation in heart on long-term follow-up (4 weeks) after treatment. Images are scanned and digitized and the volume of scar tissue quantified. Immunohistology is performed on unstained sections to show presence of Frataxin protein in multiple tissues.

Assessment of mitochondrial respiration. Mitochondrial respiration ratios will be determined using total mitochondria isolated from homozygous treated and untreated hearts and livers, and oxygen consumption measured with an oxygraph and Clark oxygen electrode (Yellow Spring Instruments, Yellow Spring, Ohio) (D. Rickwood, et al., In *Mitochondria. A Practical Approach*. V. M. Darley-Usmar, Rickwood, D., and Wilson, M. T., editors. IRL Press Limited, Oxford, England. 1-16 (1987)). Oxygen consumption by mitochondria is measured in air saturated medium in a closed container with a magnetic stir bar at 28° C. Atractyloside, an inhibitor of the ATP-ADP translocator, is used to show this oxygen consumption is due to mitochondrial respiration. Rat liver mitochondria are used as a second control to check the integrity of the system.

Determination of protein oxidation: Determination of protein oxidation: Reactive oxygen species attack amino acid residues in proteins to produce carbonyl functional groups. The carbonyl formation will be used as a marker for protein oxidation (P. Evans, et al., *Methods in Enzymology* 300:145-156 (1999); A. Reznick, and L. Packer, *Methods in Enzymology* 233:357-363 (1994)). 2,4-dinitrophenylhydrazine (DNPH) reacts with carbonyl groups to form protein hydrazones which are measurable spectrophotometrically. By obtaining the spectra at 355-390 nm, the concentration of hydrazones/ml can be calculated using Beer's Law: $C=A/\epsilon$, where A in the absorption and $\epsilon$ is the extinction coefficient. For DNPH, $\epsilon=45.45$ nmol/ml. Levels of manganese superoxide dismutase (MnSOD) mRNA are measured by slot blot analysis (Northern Blotting) using a cDNA probe for mouse MnSOD (Z. Chen, et al., *Journal of Molecular & Cellular Cardiology* 30:2281-2289 (1998)).

Phenotypic Assays: Animals are followed for the development of cardiomyopathy using echocardiography and growth rate, and for signs of neuromotor weakness by exercise in wheel cage and proprioception as in published data (H. Puccio, et al., *Nat. Genet.* 27:181-186 (2001)). Cardiac function is determined longitudinally by cardiac ultrasound (see FIG. 2) and ex vivo by heart to body weight. The neuroanatomy of brain from animals with advanced disease is evaluated using histology, EM, and immunohistochemistry.

The foregoing is illustrative of the present invention, and is not to be construed as limiting thereof. The invention is defined by the following claims, with equivalents of the claims to be included therein.

That which is claimed is:

1. A conjugate, consisting of:
   (a) an HIV-TAT protein transduction domain peptide comprising at least about four sequential amino acid residues of SEQ ID NO:1;
   (b) a protein or peptide of interest; and
   (c) a mitochondrial targeting sequence linking said protein transduction domain peptide and said protein or peptide of interest, wherein said targeting sequence is cleavable within the mitochondrial matrix of a target cell into which said protein or peptide of interest is delivered, wherein said mitochondrial targeting sequence is a mitochondrial malate dehydrogenase cleavage sequence and said protein or peptide of interest is Frataxin.

* * * * *

SEQUENCE LISTING

<160> NUMBER OF SEQ ID NOS: 9

<210> SEQ ID NO 1
<211> LENGTH: 36
<212> TYPE: PRT
<213> ORGANISM: Human immunodeficiency virus

```
<400> SEQUENCE: 1

Cys Phe Ile Thr Lys Ala Leu Gly Ile Ser Tyr Gly Arg Lys Lys Arg
1               5                   10                  15

Arg Gln Arg Arg Arg Pro Pro Gln Gly Ser Gln Thr His Gln Val Ser
            20                  25                  30

Leu Ser Lys Gln
        35

<210> SEQ ID NO 2
<211> LENGTH: 10
<212> TYPE: PRT
<213> ORGANISM: Human immunodeficiency virus

<400> SEQUENCE: 2

Gly Arg Lys Lys Arg Arg Gln Arg Arg Arg
1               5                   10

<210> SEQ ID NO 3
<211> LENGTH: 11
<212> TYPE: PRT
<213> ORGANISM: Human immunodeficiency virus

<400> SEQUENCE: 3

Tyr Gly Arg Lys Lys Arg Arg Gln Arg Arg Arg
1               5                   10

<210> SEQ ID NO 4
<211> LENGTH: 11
<212> TYPE: PRT
<213> ORGANISM: Artificial
<220> FEATURE:
<223> OTHER INFORMATION: Synthetic PTD sequence

<400> SEQUENCE: 4

Tyr Ala Arg Ala Ala Ala Arg Gln Ala Arg Ala
1               5                   10

<210> SEQ ID NO 5
<211> LENGTH: 21
<212> TYPE: PRT
<213> ORGANISM: Artificial
<220> FEATURE:
<223> OTHER INFORMATION: Synthetic PTD sequence

<400> SEQUENCE: 5

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 6
<211> LENGTH: 27
<212> TYPE: PRT
<213> ORGANISM: Artificial
<220> FEATURE:
<223> OTHER INFORMATION: Synthetic PTD sequence

<400> SEQUENCE: 6

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

```
<210> SEQ ID NO 7
<211> LENGTH: 16
<212> TYPE: PRT
<213> ORGANISM: Drosophila melanogaster

<400> SEQUENCE: 7

Arg Gln Ile Lys Ile Trp Phe Gln Asn Arg Arg Met Lys Trp Lys Lys
1               5                   10                  15

<210> SEQ ID NO 8
<211> LENGTH: 34
<212> TYPE: PRT
<213> ORGANISM: herpes simplex virus type 1

<400> SEQUENCE: 8

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 9
<211> LENGTH: 13
<212> TYPE: PRT
<213> ORGANISM: Artificial
<220> FEATURE:
<223> OTHER INFORMATION: TAT-mMDH-eGFP fusion protein sequence

<400> SEQUENCE: 9

Gly Tyr Gly Arg Lys Lys Arg Arg Gln Arg Arg Arg Gly
1               5                   10
```